(12) United States Patent
Pitner et al.

(10) Patent No.: US 11,904,026 B2
(45) Date of Patent: *Feb. 20, 2024

(54) METALLOHYDROPORPHYRINS FOR PHOTOACOUSTIC IMAGING

(71) Applicant: NIRvana Sciences Inc., Durham, NC (US)

(72) Inventors: James Bruce Pitner, Durham, NC (US); Russell D. Thomas, Wake Forest, NC (US); Joshua O. Akhigbe, Durham, NC (US)

(73) Assignee: NIRvana Sciences Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/140,920

(22) Filed: Jan. 4, 2021

(65) Prior Publication Data

US 2021/0361783 A1 Nov. 25, 2021

Related U.S. Application Data

(63) Continuation-in-part of application No. 16/483,394, filed as application No. PCT/US2018/016672 on Feb. 2, 2018.

(60) Provisional application No. 62/454,493, filed on Feb. 3, 2017.

(51) Int. Cl.
*A61K 49/22* (2006.01)
*A61B 5/00* (2006.01)
*G01N 29/24* (2006.01)

(52) U.S. Cl.
CPC .......... *A61K 49/221* (2013.01); *A61B 5/0095* (2013.01); *G01N 29/2418* (2013.01); *G01N 2291/02466* (2013.01)

(58) Field of Classification Search
None
See application file for complete search history.

(56) References Cited

U.S. PATENT DOCUMENTS

| | | | |
|---|---|---|---|
| 6,376,483 B1 | 4/2002 | Robinson | |
| 6,559,374 B2 | 5/2003 | Lindsey et al. | |
| 6,913,935 B1 | 7/2005 | Thomas | |
| 6,946,533 B2 | 9/2005 | Grubbs et al. | |
| 7,064,103 B2 | 6/2006 | Pitner et al. | |
| 7,332,599 B2 | 2/2008 | Yu et al. | |
| 7,408,058 B2 | 8/2008 | Lindsey et al. | |
| 7,423,160 B2 | 9/2008 | Lindsey et al. | |
| 7,470,785 B2 | 12/2008 | Lindsey et al. | |
| 7,501,508 B2 | 3/2009 | Lindsey et al. | |
| 7,534,807 B2 | 5/2009 | Kim et al. | |
| 7,553,977 B2 | 6/2009 | Lindsey et al. | |
| 7,582,751 B2 | 9/2009 | Lindsey et al. | |
| 7,678,900 B2 | 3/2010 | Lindsey et al. | |
| 7,745,618 B2 | 6/2010 | Kiper et al. | |
| 7,947,828 B2 | 5/2011 | Yu et al. | |
| 7,947,829 B2 | 5/2011 | Kiper et al. | |
| 7,994,312 B2 | 8/2011 | Lindsey et al. | |
| 8,080,653 B2 | 12/2011 | Lindsey et al. | |
| 8,097,609 B2 | 1/2012 | Borbas et al. | |
| 8,173,691 B2 | 5/2012 | Kim et al. | |
| 8,173,692 B2 | 5/2012 | Kim et al. | |
| 8,187,824 B2 | 5/2012 | Lindsey | |
| 8,207,329 B2 | 6/2012 | Lindsey et al. | |
| 8,664,260 B2 | 3/2014 | Kim et al. | |
| 9,303,165 B2 | 4/2016 | Lindsey et al. | |
| 9,365,722 B2 | 6/2016 | Lindsey et al. | |
| 2002/0155520 A9 | 10/2002 | Lichtman et al. | |
| 2003/0167002 A1 | 9/2003 | Nagar et al. | |
| 2008/0019921 A1 | 1/2008 | Zhang | |
| 2010/0084610 A1 | 4/2010 | Ftime et al. | |
| 2012/0322999 A1 | 12/2012 | Lindsey et al. | |
| 2014/0371286 A1 | 12/2014 | Kim et al. | |
| 2015/0316511 A1 | 11/2015 | Guo | |
| 2016/0077083 A1 | 3/2016 | Teich et al. | |
| 2016/0082127 A1 | 3/2016 | Lai et al. | |
| 2016/0082134 A1 | 3/2016 | Prud Homme et al. | |
| 2019/0085237 A1 | 3/2019 | Miteva | |
| 2019/0264102 A1 | 8/2019 | Pitner et al. | |
| 2020/0009272 A1 | 1/2020 | Pitner et al. | |

FOREIGN PATENT DOCUMENTS

| | | |
|---|---|---|
| CN | 101940948 B | 1/2011 |
| WO | WO 2000/073308 | 12/2000 |
| WO | WO 2002/000662 | 1/2002 |
| WO | WO 2002/009196 | 1/2002 |
| WO | WO 2007/064841 | 6/2007 |
| WO | WO 2015/084270 | 6/2015 |
| WO | WO 2016/178191 A1 | 11/2016 |
| WO | WO 2017/214637 A1 | 12/2017 |
| WO | WO 2018/144886 A1 | 8/2018 |

(Continued)

OTHER PUBLICATIONS

Abuteen et al., "The evaluation of NIR-absorbing porphyrin derivatives as contrast agents in photoacoustic imaging," Phys.Chem. Chem. Phys., 2013, 15, 18502.

(Continued)

*Primary Examiner* — Jennifer Chin
(74) *Attorney, Agent, or Firm* — Jenkins, Taylor & Hunt P.A.,

(57) ABSTRACT

Provided are photoacoustic imaging contrast agents that include at least one radiation-absorbing component comprising a copper-complexed and/or manganese-complexed chlorin and/or bacteriochlorin and/or a derivative thereof, or a combination thereof. Also provided are methods for using the disclosed photoacoustic imaging contrast agents either singly or in combination for generating an image of a volume, optionally a subject or a body part, cell, tissue, or organ thereof. Further provided are compositions and methods for multiplex photoacoustic imaging of a volume, optionally a subject or a body part, cell, tissue, or organ thereof using photoacoustic imaging contrast agents that include a plurality of the presently disclosed copper-complexed and/or manganese-complexed chlorins and/or bacteriochlorins and/or derivatives thereof simultaneously.

19 Claims, 8 Drawing Sheets

(56) References Cited

OTHER PUBLICATIONS

Chen et al., "Synthesis and Physicochemical Properties of Metallobacteriochlorins," Inorganic Chemistry, vol. 51, No. 17, pp. 9443-9464 (Jan. 1, 2012), XP055466897.
De Zerda et al., "Family of Enhanced Photoacoustic Imaging Agents for High Sensitivity and Multiplexing Studies in Living Mice," ACS Nano. Jun. 26, 2012; 6(6): 4694-4701.
European Search Report corresponding to European Patent Application No. 17811169.6 dated Jan. 8, 2020.
Extended European Search Report corresponding to European Patent Application No. 17811169.6 dated May 26, 2020.
Extended European Search Report corresponding to European Patent Application No. 18747932.4 dated Feb. 4, 2021.
Fan et al. "Regioselective 15-Bromination and Functionalization of a Stable Synthetic Bacteriochlorin", J Org Chem. 2007. vol. 72(14), pp. 5350-5357, entire document.
Hu et al. (2016) Panchromatic chromophore-tetrapyrrole light-harvesting arrays constructed from Bodipy, perylene, terrylene, porphyrin, chlorin, and bacteriochlorin building blocks. New J Chem 40:8032-8052.
International Preliminary Report on Patentability corresponding to International Application No. PCT/US2017/037073 dated Dec. 11, 2018.
International Preliminary Report on Patentability corresponding to International Application No. PCT/US2018/016672 dated Aug. 6, 2019.
International Search Report corresponding to International Application No. PCT/US2017/037073 dated Aug. 28, 2017.
International Search Report corresponding to International Application No. PCT/US2018/016672 dated Mar. 28, 2018.
International Search Report corresponding to International Application No. PCT/US2020/033606 dated Oct. 1, 2020.
International Search Report corresponding to International Application No. PCT/US2020/033627 dated Sep. 30, 2020.
Jiang et al., "Hydrophilic tetracarboxy bacteriochlorins for photonics applications," Org. Biomol. Chem., 2014, 12, 86.
Jiang et al., "Hydrophilic tetracarboxy bacteriochlorins for photonics applications," The Royal Society of Chemistry, pp. S1-S81 (2013).
Jiang et al., "Polarity-tunable and wavelength-tunable bacteriochlorins bearing a single carboxylic acid or NHS ester. Use in a protein bioconjugation model system," New J. Chem., 2015, 39, 403.
Laha et al., "Synthetic Chlorins Bearing Auxochromes at the 3- and 13-Positions," J. Org. Chem. 2006, 71, 4092-4102.
Lee et al., Preparation of Self-Assembled Crystalline Microparticles with Bispyridyl Zn-Porphyrin, Bulletin Korean Chemical Society 33(4), pp. 1317-1320, 2012.
Lindsey (2015) De Novo Synthesis of Gem-Dialkyl Chlorophyll Analogues for Probing and Emulating our Green World. Chem Rev 115:6534-6620.
Liu et al., "Bioconjugatable, PEGylated hydroporphyrins for photochemistry and photomedicine. Narrow-band, red-emitting chlorins," The Royal Society of Chemistry and the Centre National de la Recherche Scientifique (2016).
Luciano et al. "Modifications of Porphyrins and Hydroporphyrins for Their Solubilization in Aqueous Media", Molecules. 2017. vol. 22, pp. 980, entire document.
Madison et al. (1990) Latex nanosphere delivery system (LNDS): novel nanometer-sized carriers of fluorescent dyes and active agents selectively target.
Muthiah et al. (2008) Synthesis and Excited-state Photodynamics of a Chlorin-Bacteriochlorin Dyad—Through-space Versus Through-bond Energy Transfer in Tetrapyrrole Arrays. Photochem Photobiol 84:786-801.
Office Action corresponding to Japanese Patent Application No. 2019517192 dated Feb. 15, 2021. Translation.
Office Action corresponding to U.S. Appl. No. 16/308,285 dated Mar. 22, 2021.
Office Action corresponding to U.S. Appl. No. 16/483,394 dated Jun. 10, 2021.
Office Action corresponding to U.S. Appl. No. 16/483,394 dated Oct. 29, 2020.
Partial Supplementary European Search Report corresponding to European Patent Application No. 17811169.6 dated Jan. 8, 2020.
Pilch et al., "Molecular symmetry determines the mechanism of a very efficient ultrafast excitation-to-heat conversion in Ni-substituted chlorophylls," Biochimica et Biophysica Acta 1827 (2013) 30-37.
Pitner et al., "Chlorins: A novel family of violet laser-excitable red to far-red fluorophores for polychromatic flow cytometry," submitted Feb. 17, 2016.
Ptaszek et al., "Near-infrared molecular imaging probes based on chlorin-bacteriochlorin dyads," Proc. of SPIE vol. 7576, 75760E-1-75760E-9 (2010).
Ruzie et al. "Tailoring a Bacteriochlorin Building Block with Cationic, Amphipathic, or Lipophilic Substituents", J. Org. Chem. 2008. vol. 73, pp. 5806-5820, entire document, especially: p. 5814, Table 2, Entry 2, Product BC-16.
Schaberle et al., "Multi-spectral photoacoustic mapping of bacteriochlorins diffusing through the skin: exploring a new PAT contrast agent," Molecular Imaging III, SPIE, 1000 20th St., Bellingham WA 98225-6705 USA, vol. 8089, No. 1, pp. 1-8 (Jun. 9, 2011), XP060015394.
Spagnul et al. Immobilized photosensitizers for antimicrobial applications. J. Photochemistry & photobiology, 2015, vol. 150, pp. 11-130. (Year: 2015).
Sun et al. (2013) Synthesis and Characterization of Lipophilic, Near-Infrared Absorbing Metallobacteriochlorins Chem J Chin Univ 34:776-781.
Taniguchi et al. (2008) Accessing the near-infrared spectral region with stable, synthetic, wavelength-tunable bacteriochlorins. New J Chem 32:947-958.
Written Opinion of the International Searching Authority corresponding to International Application No. PCT/US2017/037073 dated Aug. 18, 2017.
Written Opinion of the International Searching Authority corresponding to International Application No. PCT/US2018/016672 dated Mar. 28, 2018.
Written Opinion of the International Searching Authority corresponding to International Application No. PCT/US2020/033606 dated Oct. 1, 2020.
Written Opinion of the International Searching Authority corresponding to International Application No. PCT/US2020/033627 dated Sep. 30, 2020.
Wu et al.,"Squaraine-Based Polymer Dots with Narrow, Bright Near-Infrared Fluorescence for Biological Applications," J. Am. Chem. Soc. 2015, 137, 173-178.
Yang et al. (2011) Photophysical Properties and Electronic Structure of Stable, Tunable Synthetic Bacteriochlorins: Extending the Features of Native Photosynthetic Pigments. J Phys Chem B 115:10801-10816.
Yu et al. (2014) Strongly Conjugated Hydroporphyrin Dyads: Extensive Modification of Hydroporphyrins' Properties by Expanding the Conjugated System. J Org Chem 79:7910-7925.
Yu et al., "Near-IR Emissive Chlorin-Bacteriochlorin Energy-Transfer Dyads with a Common Donor and Acceptors with Tunable Emission Wavelength," J. Org. Chem. 2013, 78, 10678-10691.
Zhang et al., "Bioconjugatable, PEGylated hydroporphyrins for photochemistry and photomedicine. Narrow-band, near-infrared-emitting bacteriochlorins," NewJ.Chem., 2016, 40, 7750.
Decision to Grant corresponding to Japanese Patent Application No. 2019517192 dated Jan. 31, 2022.
International Search Report corresponding to International Application No. PCT/US2022/011120 dated May 18, 2022.
Notice of Publication Corresponding to Patent Application Serial No. 2019-517192 dated Mar. 3, 2022.
Notice of Publication Corresponding to Patent Application Serial No. 208108068-1105 dated Feb. 2, 2022.
Notice of Publication Corresponding to U.S. Appl. No. 17/612,971 dated Aug. 11, 2022.

(56) References Cited

OTHER PUBLICATIONS

Office Action and Search Report corresponding to Chinese Patent Application No. 201780043650.6 dated Dec. 3, 2021. Translations.
Office Action corresponding to Chinese Patent Application No. 201880019863.X dated Nov. 2, 2021. Translation.
Office Action corresponding to Chinese Patent Application No. 201880019863.X dated Jul. 4, 2022. Translation.
Office Action corresponding to Chinese Patent Application No. 201880019863.X dated Sep. 5, 2022.
Office Action corresponding to European Patent Application No. 17811169.6 dated Oct. 19, 2022.
Office Action corresponding to Japanese Patent Application No. 2019563327 dated Jan. 21, 2022.
Office Action corresponding to U.S. Appl. No. 16/308,285 dated Dec. 15, 2021.
Office Action corresponding to U.S. Appl. No. 16/483,394 dated Mar. 17, 2022.
Office Action (Final) corresponding to U.S. Appl. No. 16/483,394 dated Oct. 6, 2022.
Office Action corresponding to Patent Application Serial No. 2019-563327 dated Nov. 28, 2022.
Office Action (Non-Final) Corresponding to U.S. Appl. No. 16/308,285 dated Nov. 29, 2022.
Rakestraw et al. (1990) Antibody-targeted photolysis: in vitro studies with Sn(IV) chlorin e6 covalently bound to monoclonal antibodies using a modified dextran carrier. Proceedings of the National Academy of Science of the United States of America 87:4217-4221.
Liu et al. Chlorophyll-inspired red-region fluorophores: building block synthesis and studies in aqueous media. 2018 Molecules 23: 130: 30p.
Decision of Rejection corresponding to Chinese Patent Application No. 201880019863.X dated Dec. 22, 2022.
Decision of Rejection corresponding to Chinese Patent Application No. 201780043650.6 dated Jun. 1, 2023.
Office Action (Non-Final) corresponding to U.S. Appl. No. 16/483,394 dated May 25, 2023.
Office Action corresponding to U.S. Appl. No. 16/308,285 dated Jun. 12, 2023.
Decision of Rejection corresponding to Japanese Patent Application No. 2019-563327 dated July 4, 2023.
European Search Report corresponding to European Patent Application No. 20810806.8-1108 dated Nov. 29, 2022.

Bacteriochlorophyll a

Synthetic bacteriochlorin design

Nickel-bacteriochlorin B107

MB3

MB2

MB1

METALLOHYDROPORPHYRINS FOR PHOTOACOUSTIC IMAGING

CROSS-REFERENCE TO RELATED APPLICATION

This application is a continuation-in-part of U.S. patent application Ser. No. 16/483,394, filed Aug. 2, 2019, which itself was a U.S. National Stage Application of PCT International Patent Application Serial No. PCT/US2018/016672, filed Feb. 2, 2018, which itself claims the benefit of U.S. Provisional Patent Application Ser. No. 62/454,493, filed Feb. 3, 2017. The disclosure of each of these applications is incorporated herein by reference in its entirety.

TECHNICAL FIELD

The presently disclosed subject matter relates generally to metallohydroporphyrins and metallohydroporphyrin conjugates and derivatives, and methods for using the same as contrast agents for photoacoustic imaging. In particular, the presently disclosed subject matter relates to metallobacteriochlorins and metallochlorins and methods of using the same in photoacoustic imaging methodologies.

BACKGROUND

Photoacoustic Imaging (PAI) is an emerging medical imaging modality that is based on the phenomenon of conversion of optical energy into acoustic energy (Bell, 1880). PAI offers distinct advantages over other strictly optical imaging methods such as fluorescence because physiological tissue poses considerably less interference for acoustic waves than it does for light. Although PAI by definition still requires optical excitation and subsequent loss of light through endogenous absorption and scattering, the lower interference of the acoustic signal response allows imaging of features at much greater depths, up to 5 or even 7 cm (de Zerda et al., 2012; Wilson et al., 2013; Wang & Yao, 2016).

In addition to collecting signals from endogenous biomolecules such as melanin and hemoglobin, PAI can be used to detect both general contrast agents and targeted PAI probes. Typically, such reagents have their peak optical absorption within the near infrared (NIR) spectral region (e.g., 680-1100 nm), where biological interference is reduced. Although a few NIR reagents are in development such as IRDye 800CW (Marshall et al., 2010), quantum dots, gold nanoparticles, and carbon nanotubes (de Zerda et al., 2012) most PAI studies to date have employed either endogenous probes (e.g., melanin or hemoglobin) or the exogenous probe Indocyanine Green (ICG), a carbocyanine dye which has received regulatory approval but suffers from a significantly broad absorption spectrum (see FIG. 1). ICG's broad absorption spectrum leads to a corresponding broad PAI signal that limits the number of additional targeted biomarkers that can be distinguished in a typical experiment when ICG is employed as the contrast agent.

Ideally, clinicians would like to measure multiple biomarkers in a single run for confirmation of complex diseases such as cancer. To make the simultaneous detection of multiple biomarkers within the NIR spectral range possible, disclosed herein are PAI reagents based on synthetic bacteriochlorins, a class of PAI agents that offer extremely narrow absorption and PAI spectra, thereby enabling multiplex detection with minimal overlap and within a compact NIR spectral window (e.g., 650-1070 nm).

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides in some embodiments photoacoustic imaging (PAI) contrast agents. In some embodiments, the PAI contrast agents comprise at least one radiation-absorbing component that comprises a metallobacteriochlorin, a metallochlorin, a derivative thereof, or any combination thereof, wherein the metallobacteriochlorin, the metallochlorin, or the derivative thereof is complexed to copper and/or manganese. In some embodiments, the PAI contrast agent comprises a plurality of different copper-complexed and/or manganese-complexed bacteriochlorins, copper-complexed and/or manganese-complexed chlorins, derivatives thereof, or combinations thereof, wherein each copper-complexed and/or manganese-complexed bacteriochlorin, copper-complexed and/or manganese-complexed chlorin, or derivative thereof has a different absorption spectrum in the range of 650-1070 nm. In some embodiments, the photoacoustic imaging contrast agent comprises at least three different metallobacteriochlorins, metallochlorins, and/or derivatives thereof, wherein each metallobacteriochlorin, metallochlorin, and/or derivative thereof has an absorption spectrum with a peak absorption value in the range of 700-950 nm; and the at least three absorption spectra are substantially non-overlapping in the range of 700-950 nm. In some embodiments, the metallobacteriochlorin and/or metallochlorin comprises a metal selected from the group consisting of zinc, copper, nickel, iron, cobalt, manganese, and copper. In some embodiments, the metallobacteriochlorin and/or metallochlorin comprises copper and/or manganese. In some embodiments, the photoacoustic imaging contrast agent comprises at least one copper-complexed bacteriochlorin, copper-complexed chlorin, and/or derivative thereof, and at least one additional metallobacteriochlorin, metallochlorin, and/or derivative thereof complexed to a metal selected from the group consisting of zinc, nickel, iron, manganese, and cobalt.

The presently disclosed subject matter also provides in some embodiments methods for generating an image of a volume or a part thereof. In some embodiments, the methods comprise administering to the volume or the part thereof a contrast agent comprising at least one radiation-absorbing component comprising a metallobacteriochlorin, a metallochlorin, or a derivative thereof, wherein the metallobacteriochlorin, the metallochlorin, and/or the derivative thereof is complexed to copper and/or manganese; exposing the volume or the part thereof to radiation; detecting ultrasonic waves generated in the volume or the part thereof by the radiation; and generating a photoacoustic image therefrom of the volume or the part thereof containing the administered contrast agent. In some embodiments, the metallobacteriochlorin, the metallochlorin, and/or the derivative thereof is a component of and/or encapsulated in a micelle, a liposome, a nanoparticle, or a combination thereof. In some embodiments, radiation with a wavelength of 650-1070 nm is used. In some embodiments, radiation with a wavelength of 650-900 nm, 700-950 nm, and/or 750-950 nm is used. In some embodiments, the physiologically tolerable contrast agent comprises a plurality of different metallobacteriochlorins, metallochlorins, derivatives thereof, and/or combinations thereof, each metallobacteriochlorin, metallochlorin, and/or the derivative thereof having a different absorption spectrum in the range of 650-1070 nm. In some embodiments, the contrast agent comprises a targeting agent. In some embodiments, the targeting agent comprises a moiety that binds to a ligand and/or a target present on a tumor cell or a cancer cell, or a vascular endothelial cell associated therewith. In some embodiments, the ligand and/or a target comprises a tumor-associated antigen. In some embodiments, the moiety comprises a peptide or peptide mimetic that binds to a tumor-associated antigen.

The presently disclosed subject matter also provides in some embodiments methods for multiplex photoacoustic imaging of a volume or a part thereof. In some embodiments, the methods comprise administering to the volume or the part thereof a contrast agent comprising a plurality of radiation-absorbing components, each member of the plurality of radiation-absorbing components comprising a metallobacteriochlorin, a metallochlorin, and/or a derivative thereof, wherein the metallobacteriochlorin, the metallochlorin, and/or the derivative thereof is complexed to copper and/or manganese; exposing the volume or a part thereof to radiation, wherein the radiation is calibrated to wavelengths that are differentially absorbed by the plurality of radiation-absorbing components; differentially detecting ultrasonic waves generated in the volume or the part thereof by the radiation as it is differentially absorbed by the plurality of radiation-absorbing components; and generating a photoacoustic image therefrom of the volume or the part thereof containing the administered contrast agent, wherein the photoacoustic image is generated from the differentially detecting ultrasonic waves. In some embodiments, one or more of the plurality of the metallobacteriochlorins, the metallochlorins, and/or the derivatives thereof is a component of and/or encapsulated in a micelle, a liposome, a nanoparticle, or a combination thereof. In some embodiments, radiation with a wavelength of 650-1070 nm is used. In some embodiments, radiation with a wavelength of 650-900 nm, 700-950 nm, and/or 750-950 nm is used. In some embodiments, each member of the plurality of radiation-absorbing components has a different absorption spectrum in the range of 650-1070 nm. In some embodiments, one or more of the members of the plurality of radiation-absorbing components comprises a targeting agent. In some embodiments, the targeting agent comprises a moiety that binds to a ligand and/or a target present on a tumor cell or a cancer cell, or a vascular endothelial cell associated therewith. In some embodiments, the ligand and/or a target comprises a tumor-associated antigen. In some embodiments, the moiety comprises a peptide or peptide mimetic that binds to a tumor-associated antigen. In some embodiments, two or more of the members of the plurality of radiation-absorbing components comprise a targeting agent. In some embodiments, the two or more of the members of the plurality of radiation-absorbing components comprise different targeting agents. In some embodiments, the different targeting agents bind to and/or otherwise accumulate in the same or different targets and/or targeted sites.

In some embodiments of the methods of the presently disclosed subject matter, the volume is a subject or a body part thereof, optionally a cell, tissue, and/or organ thereof. In some embodiments, the volume comprises a tumor cell, a cancer cell, or a tumor- or cancer-associated vascular cell. In some embodiments, the contrast agent is a physiologically tolerable contrast agent or a plurality of physiologically tolerable contrast agents. In some embodiments, the contrast agent is physiologically tolerable for use in a human. In some embodiments, the contrast agent is provided in a pharmaceutical composition comprising the photoacoustic imaging contrast agent and a pharmaceutically acceptable carrier, diluent, or excipient. In some embodiments, the pharmaceutical composition is pharmaceutically acceptable for use in a human. In some embodiments, the volume comprises one or more targets and/or targeted sites that can be targeted by a targeting agent.

In some embodiments, the presently disclosed subject matter also provides photoacoustic imaging contrast agents. In some embodiments a photoacoustic imaging contrast agent of the presently disclosed subject matter comprises at least one radiation-absorbing component comprising a bacteriochlorin, a metallobacteriochlorin, a derivative thereof, or a combination thereof. In some embodiments, the at least one radiation-absorbing component comprises a compound selected from the group consisting of:

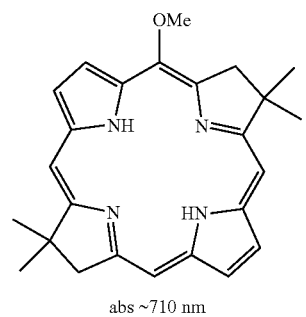

abs ~710 nm

B1

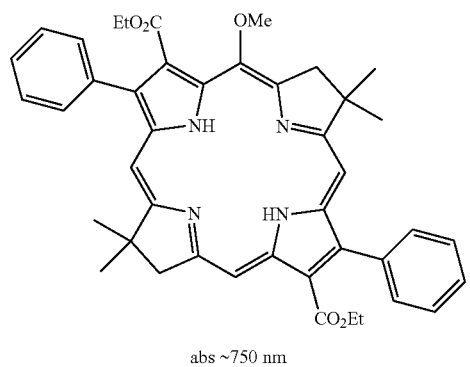

abs ~750 nm

B2

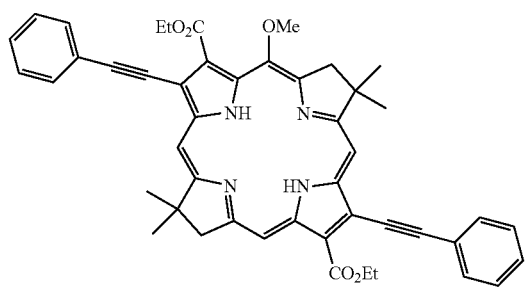

B3 abs ~790 nm

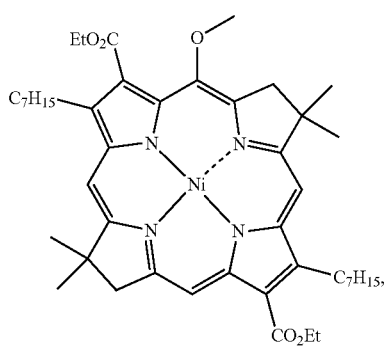

B107

In some embodiments, the at least one radiation-absorbing component comprises a derivative of B1-B3 and B107 comprising a complexed metal, wherein the complexed metal is selected from the group consisting of zinc, copper, manganese, nickel, cobalt, and iron. In some embodiments, the complexed metal is copper and/or manganese. In some embodiments, the derivative comprises a compound selected from the group consisting of:

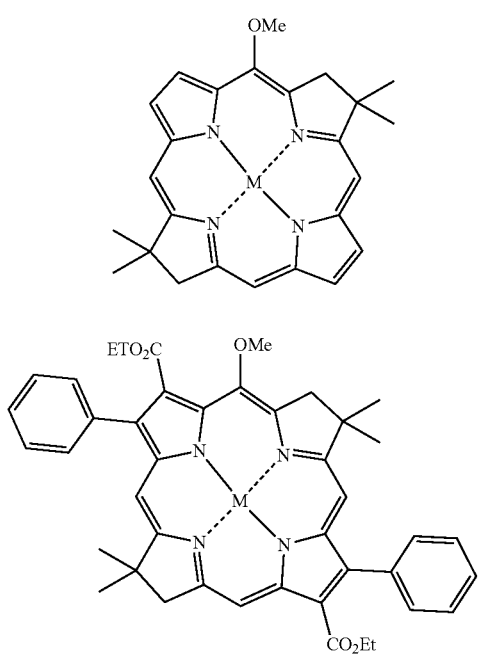

MB1

MB2 and

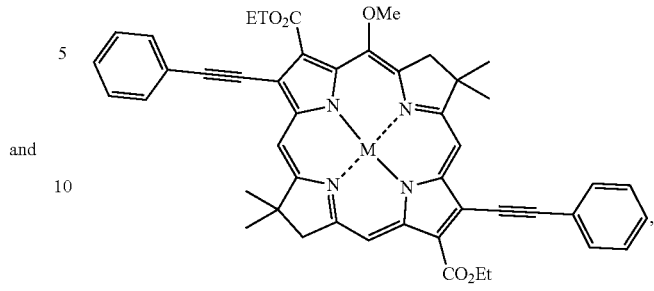

MB3 and wherein M is a metal, optionally a metal selected from the group consisting of zinc, copper, manganese, nickel, cobalt, and iron. In some embodiments, the complexed metal is copper and/or manganese. In some embodiments, the at least one radiation-absorbing component comprises a compound selected from the group consisting of MBC-1, MBC-2, and MBC-3, wherein MBC-1, MBC-2, and MBC-3 have the following structures:

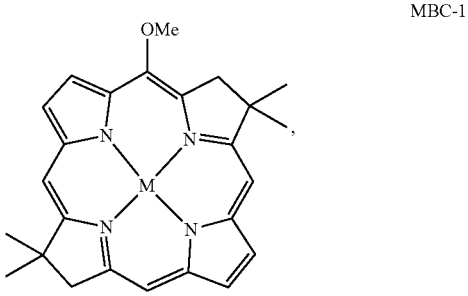

MBC-1

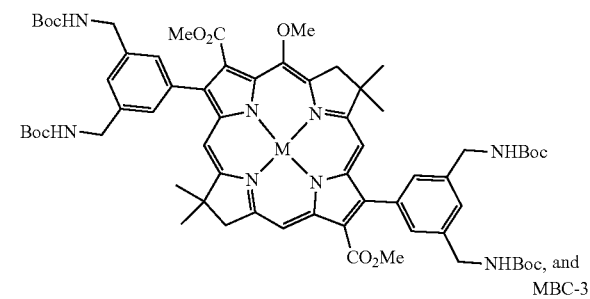

MBC-2

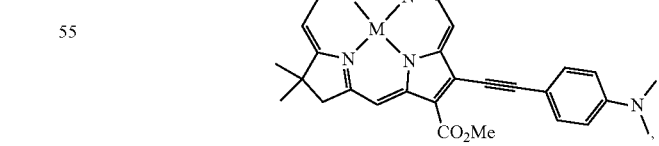

MBC-3 and further wherein M is a metal selected from the group consisting of zinc (Zn), nickel (Ni), iron (Fe), cobalt (Co), manganese (Mn) and copper (Cu). In some embodiments, the at least one radiation-absorbing component comprises CuBC-725, CuBC-775, or CuBC-840, wherein CuBC-725, CuBC-775, and CuBC-840 have the following structures:

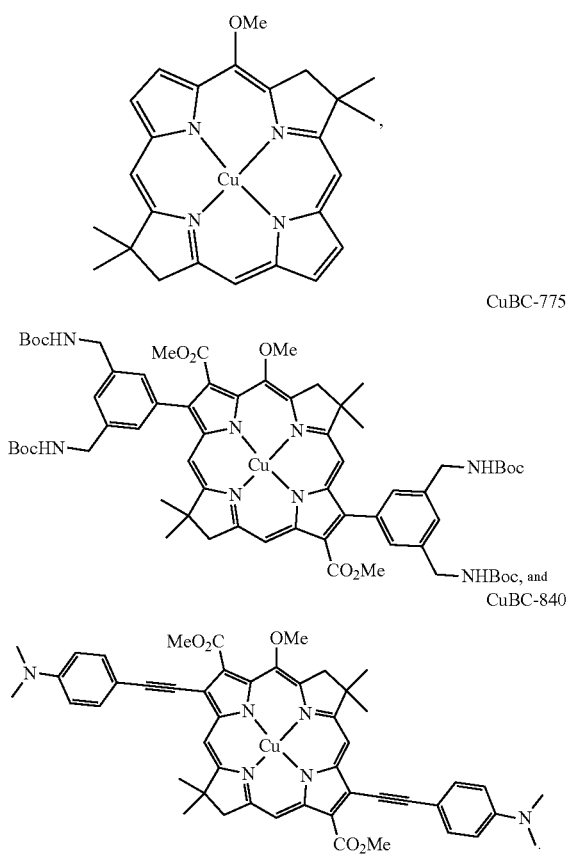

In some embodiments, the photoacoustic imaging contrast agent is physiologically tolerable for use in a subject, optionally a human.

In some embodiments, the presently disclosed subject matter provides pharmaceutical compositions. In some embodiments, the presently disclosed pharmaceutical compositions comprise one or more photoacoustic imaging contrast agents as described herein and a pharmaceutically acceptable carrier, diluent, or excipient. In some embodiments, the pharmaceutical composition is pharmaceutically acceptable for use in a human.

These and other aspects and embodiments which will be apparent to those of skill in the art upon reading the present disclosure, which provides the art with compositions and methods useful for detecting and/or labeling biological molecules and/or cells, particularly in the context of photoacoustic imaging and/or Multispectral Optoacoustic Tomography (MSOT).

BRIEF DESCRIPTION OF THE FIGURES

FIG. 9B shows the structures of exemplary copper-complexed metallobacteriochlorins CuBC-725, CuBC-775, and CuBC-840, which correspond to copper-complexed versions of metallobacteriochlorins MBC-1, MBC-2, and MBC-3, respectively.

DETAILED DESCRIPTION

Figure 1:
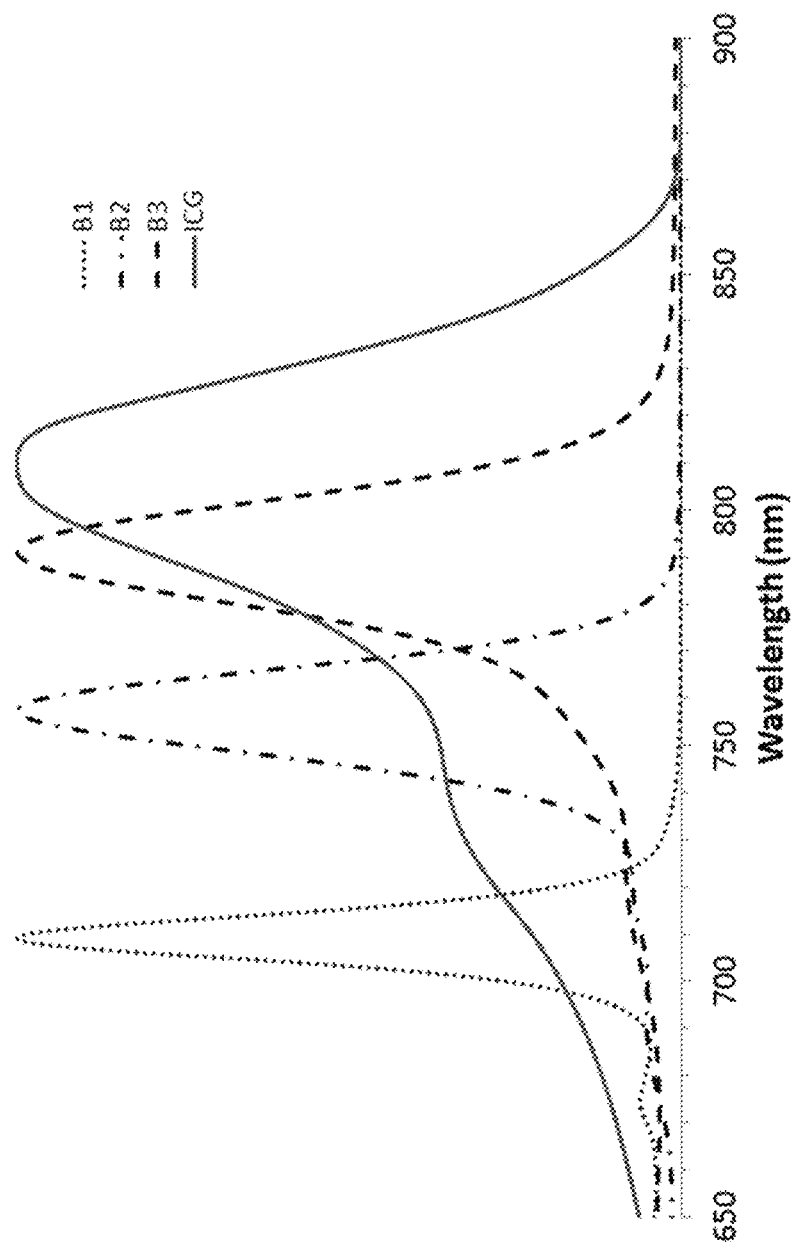
FIG. 1 is a plot of absorption spectra for ICG in water (adapted from Landsman et al., 1976) vs. a panel of three bacteriochlorins in toluene. In this example, the spectrum for B2 (2,12-diphenyl) is represented by that of the similar 2,12-dimesityl bacteriochlorin (from Chen et al., 2012).

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

I. Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and the claims should be read with the understanding that such combinations are entirely within the scope of the presently disclosed subject matter and claims.

Following long-standing patent law convention, the terms "a", "an", and "the" refer to "one or more" when used in this application, including the claims. Thus, for example, reference to "a PAI contrast agent" includes a plurality of PAI contrast agents, and so forth.

As used herein, the term "about," when referring to a value or to an amount of mass, weight, time, volume, concentration, or percentage is meant to encompass variations of in some embodiments, ±20%, in some embodiments ±10%, in some embodiments ±5%, in some embodiments ±1%, and in some embodiments ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the recited subject matter.

With respect to the terms "comprising", "consisting of", and "consisting essentially of", where one of these three terms is used herein, the presently disclosed subject matter can include the use of either of the other two terms. For example, it is understood that the scope encompassed by "comprising" can in some embodiments be broader than that encompassed by "consisting essentially of", which in some embodiments can have a scope that is broader than "consisting of". As such, it is further understood that the use of the term "comprising" also encompasses "consisting essentially of" as well as "consisting of", and the use of "consisting essentially of" also encompasses "consisting of".

As used herein, the term "bacteriochlorin" refers to a large heterocyclic aromatic ring consisting, at the core, of two pyrroles and two pyrrolines coupled through four =CH- linkages. As used herein, the term "bacteriochlorin" encompasses both bacteriochlorins and isobacteriochlorins, as well as derivatives including, but not limited to metalated derivatives. In some embodiments, a metalated derivative is a bacteriochlorin complexed to a metal selected from the group consisting of zinc, nickel, iron, cobalt, and copper. In some embodiments, the metal is copper.

As used herein, the phrase "photoacoustic imaging contrast agent" refers to a composition that when contacted with a target (optionally a target present within a subject) allows the target to be imaged by photoacoustic imaging. In some embodiments, a photoacoustic imaging contrast agent comprises at least one radiation-absorbing molecule, which in some embodiments comprises a bacteriochlorin, a metallobacteriochlorin, a chlorin, a metallochlorin, a derivative thereof, or a combination thereof. In some embodiments, the metallobacteriochlorin, the metallochlorin, or the derivative thereof is complexed to a metal selected from the group consisting of zinc, nickel, iron, cobalt, and copper. In some embodiments, the metal is copper. It is noted that a radiation-absorbing molecule can itself be a photoacoustic imaging contrast agent. Thus, in those embodiments wherein a combination of different radiation-absorbing molecules are present, the composition as a whole can be considered a photoacoustic imaging contrast agent and, in some embodiments, each individual radiation-absorbing molecule can be considered a photoacoustic imaging contrast agent.

As used herein, the phrase "substantially non-overlapping" as it relates to absorption spectra means that the percent overlap of the absorption spectra being compared is in some embodiments less than 50%, in some embodiments less than 40%, in some embodiments less than 30%, in some embodiments less than 25%, in some embodiments less than 20%, in some embodiments less than 15%, in some embodiments less than 10%, and in some embodiments less than 5%. In some embodiments, the phrase "substantially non-overlapping" as it relates to absorption spectra means that the absorption spectra have peaks that differ by at least 15 nm, 20 nm, 25 nm, 30 nm, 35 nm, 40 nm, 50 nm, 55 nm, 60 nm, 65 nm, 70 nm, 75 nm, 80 nm, 85 nm, 90 nm, or 95 nm, all of which fall within the range of 650-1070 nm. Examples of absorption spectra that are substantially non-overlapping are those for B1, B2, and B3 in FIG. 1.

As used herein, the phrases "physiologically tolerable" and "pharmaceutically acceptable" refer to compositions, in some embodiments pharmaceutical compositions, that are recognized as being safe for use in a subject to which the compositions and methods of the presently disclosed subject matter are to be applied.

As used herein, the term "volume" refers to anything for which a photoacoustic image might be desired. By way of example and not limitation, a volume can be cell, tissue, or organ present in or isolated from a subject. In some embodiments, a volume can be a physiologically relevant space or cavity within a subject.

II. Compositions of the Presently Disclosed Subject Matter

Figure 2A:
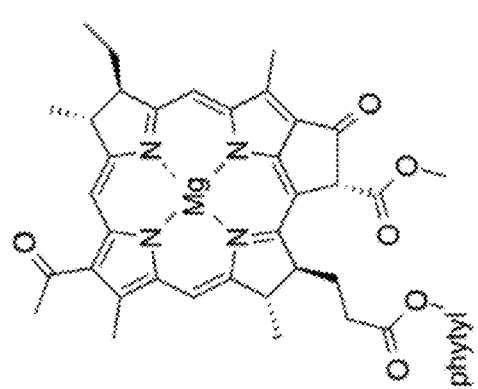
FIGS. 2A-2C are the structures of bacteriochlorophyll a (FIG. 2A) a generic design of stable wavelength-tunable tunable bacteriochlorins (FIG. 2B), and nickel-bacteriochlorin B107 (FIG. 2C).
Figure 10:
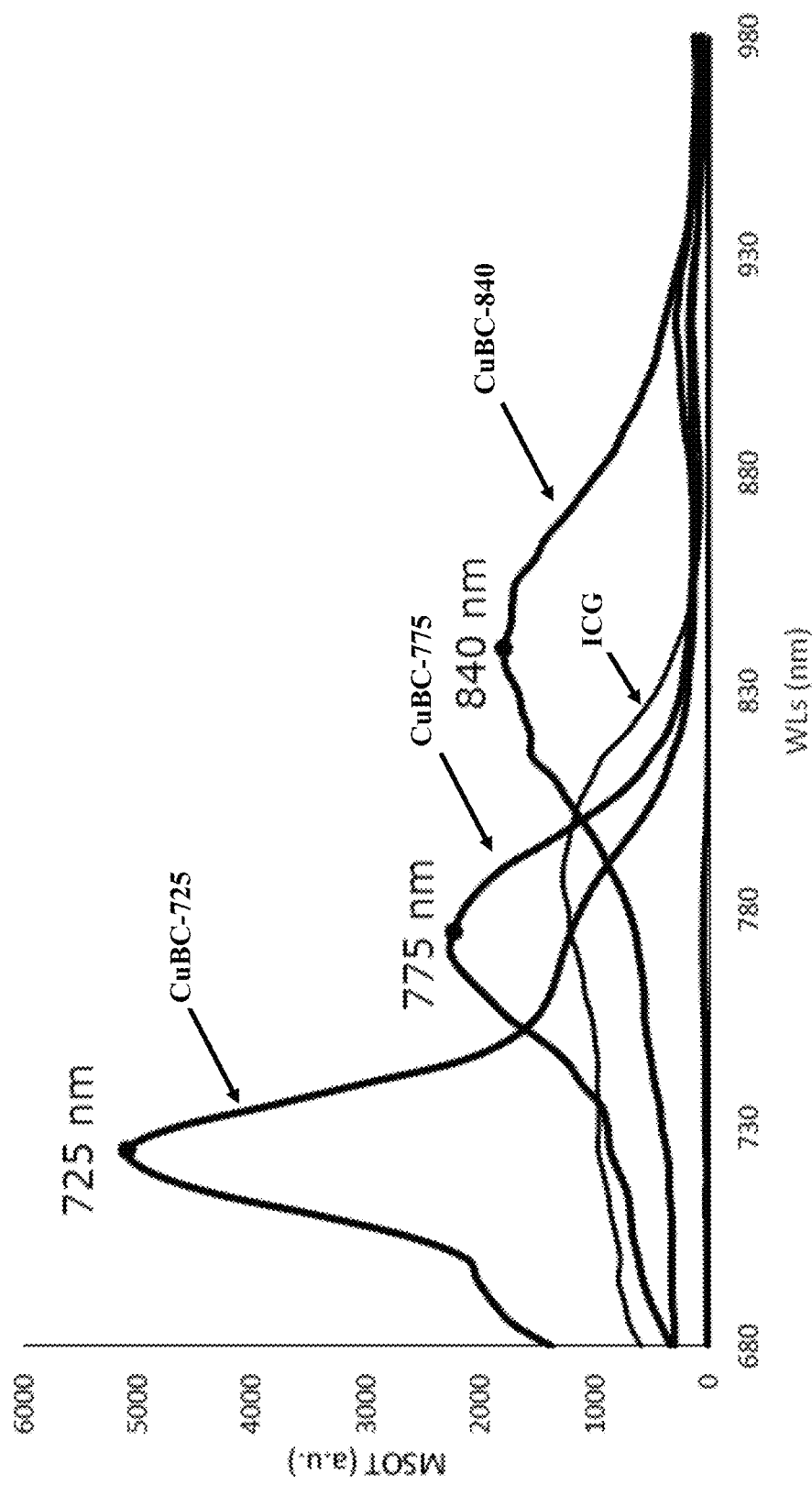
FIG. 10 is a graph showing peak absorption for CuBC-725, CuBC-775, and CuBC-840 (each at 20 μM), which occur at 725, 775, and 840 nm, respectively, in an exemplary Multispectral Optoacoustic Tomography (MSOT) experiment. ICG was tested at 20 μM as well, and each of CuBC-725, CuBC-775, and CuBC-840 outperformed ICG with respect to absorption and were characterized by narrower peaks. A phantom and water were also tested, but absorption was so low in each case that those traces are indistinguishable from the x-axis. a.u.: absorbance units.

Unlike reagents derived from naturally occurring molecules such as bacteriochlorophyll a (see FIG. 2A), completely synthetic designs of chlorins, bacteriochlorins, and derivatives thereof provide access to wavelength-tunable chlorins and bacteriochlorins (Taniguchi et al., 2008). An advantage of being able to synthetically design chlorins, bacteriochlorins, and derivatives thereof is that this facilitates development of a palette of NIR reagents with exceptionally narrow absorption bands that have distinct benefits for PAI. Based on the designation of full-width-half-max (fwhm) to describe the width of a dye's absorption, a chlorin and/or bacteriochlorin's NIR absorption band fwhm is typically less than or equal to 25 nm. Since the absorption maxima and other spectral properties of synthetic chlorins and bacteriochlorins can be readily "tuned", a portfolio of matched chlorins, bacteriochlorins, and derivatives thereof can be designed to fit within a smaller spectral range with minimal overlap between the dyes. FIG. 1 illustrates the difference between absorption spectra of three exemplary bacteriochlorins (B1-B3) and that of ICG. FIG. 10 illustrates the difference between absorption spectra of three exemplary metallobacteriochlorins (CuBC-725, CuBC-775, and CuBC-840) and that of ICG. Within the spectral space normally allotted to ICG detection, one could potentially detect up to three bacteriochlorins due to their narrow absorption profiles with minimal spectral overlap. These advantages will allow more complex analyses of multiple disease-specific biomarkers in the same experiment and ultimately accelerate the development of multiplex clinical assays based on PAI.

Figure 2B:
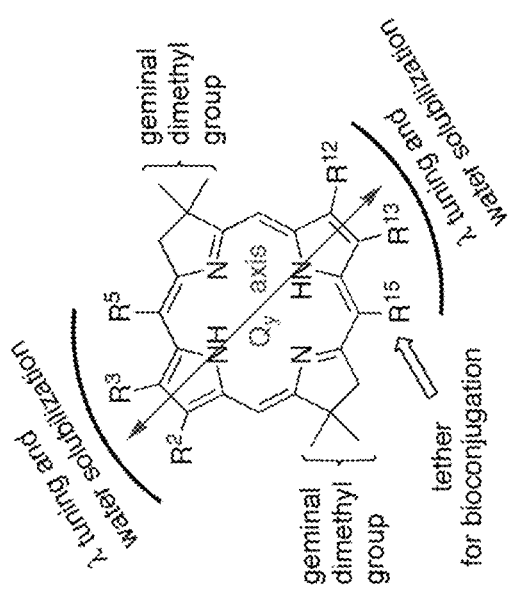
Figure 2C:
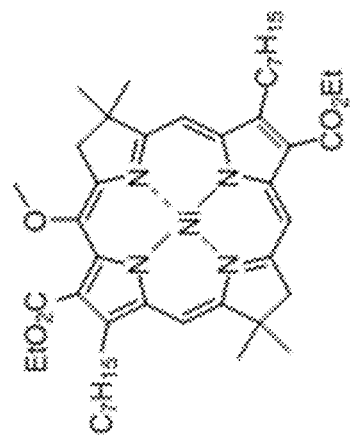

Bacteriochlorins are exemplified by bacteriochlorophyll a (see FIG. 2A), a natural product which is not readily amenable to extensive synthetic modification because of the presence of numerous (hydrophobic) substituents and chiral centers. Its reduced pyrrole rings are also subject to dehydrogenation during synthetic manipulations. However, a series of recent synthetic advances have provided access to stable, tailorable bacteriochlorins. The presence of a geminal dimethyl group in the reduced pyrroline ring blocks dehydrogenation or oxidative processes, affording a highly resilient bacteriochlorin (FIG. 2B). By introducing various groups at the beta-pyrrole positions (R2, R3, R12, R13 of FIG. 2B) and at meso-positions (R5, R15 of FIG. 2B) the absorption maxima can be readily manipulated to provide desired absorptions anywhere from 700 nm to greater than 900 nm.

Figures 3A, 3B:
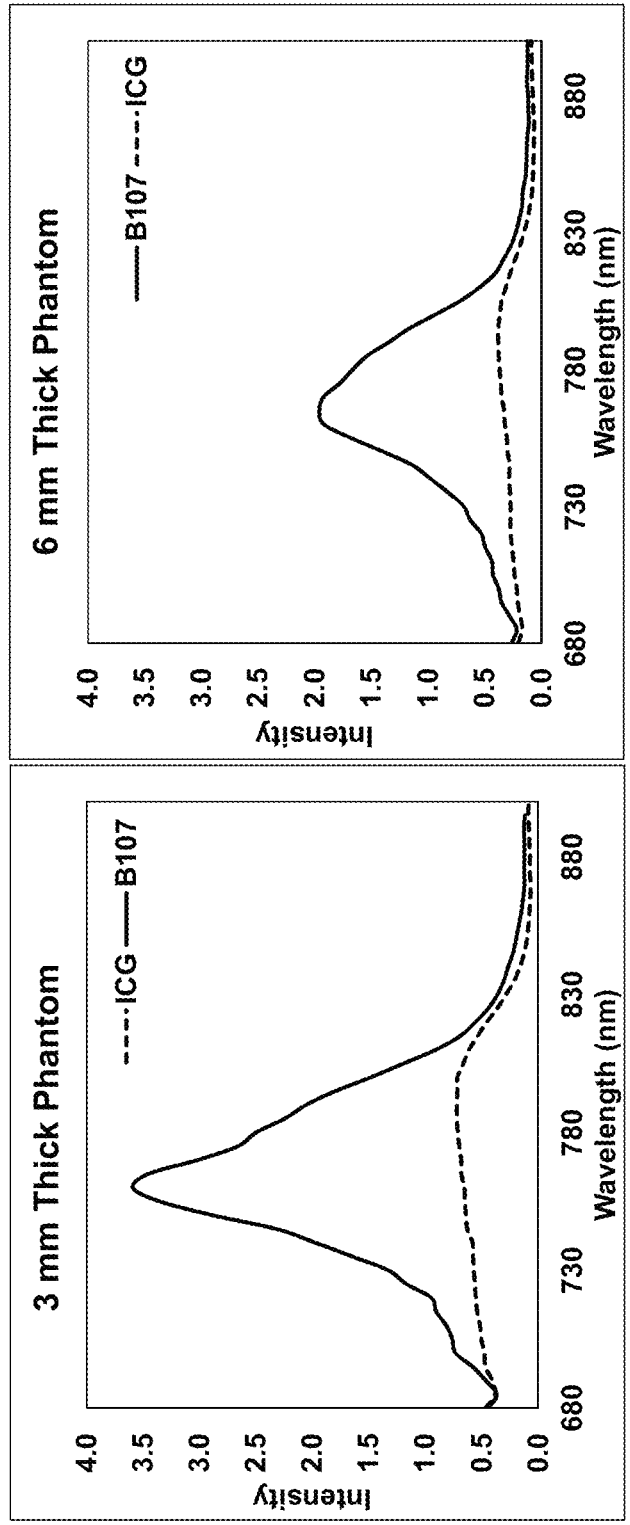
FIGS. 3A and 3B are plots comparing ICG (dashes) and Ni-metallobacteriochlorin B107 (solid line) signals imaged in agar phantoms at a depth of 3 mm (FIG. 3A) or 6 mm (FIG. 3B). Samples were introduced at equal optical density (7.5 OD) at the respective dye maxima (795 and 765 nm).

A second compelling advantage of chlorins and bacteriochlorins for PAI is shown by results described herein that demonstrate a substantial increase in PAI signal by complexing chlorins and bacteriochlorins with metals, including but not limited to copper, zinc, nickel, palladium, copper, cobalt, manganese, and others. Free base bacteriochlorins and several metallobacteriochlorins (Zn, Pd) typically display fluorescence with quantum yields ($\Phi(f)$) ranging up to 0.25, and in some cases substantial triplet states (up to 0.80 $\Phi(isc)$). It is believed that the nickel-bacteriochlorin complex has an extremely rapid non-radiative decay of its singlet state (ultrafast dynamics of B107 suggest its decay to the ground state to be ~10 ps) with essentially no conversion to its triplet state occurring. Without wanting to be bound by any specific mechanism of action, it is hypothesized that because the excited state is so short-lived, this further enhances the PAI signal. Although these properties have been recognized previously and reported in studies that characterized nickel derivatives of chlorophyll and bacteriochlorophyll (Pilch et al., 2013), attempts to produce and characterize PAI reagents with molecules of such a design has not been reported. This is undoubtedly due to the aforementioned difficulty of synthetic manipulation of bacteriochlorophyll a and other natural products. FIG. 3 shows PAI data for a nickel-bacteriochlorin (B107) in comparison to ICG using agar phantoms and a commercial PAI system with a tunable laser scanning from 680-970 nm. It was determined that this compound displayed a five-fold stronger signal compared to ICG of an equivalent optical density at two depths of agar. This greatly enhanced signal intensity suggested that PAI with targeted probes could be done at substantially greater tissue depths than those currently accessible with ICG. The data is summarized in Table 1.

TABLE 1

PAI Signal Intensity at Indicated Wavelengths for Ni-Bacteriochlorin and ICG Implanted in Agar Phantoms at Different Surface Depths

| Depth | Dye | Max (nm) | Intensity |
|---|---|---|---|
| 6 mm | ICG | 795 | 0.38 |
|  | Ni-BC | 765 | 1.96 |
| 3 mm | ICG | 790 | 0.72 |
|  | Ni-BC | 760 | 3.50 |

Figure 4:
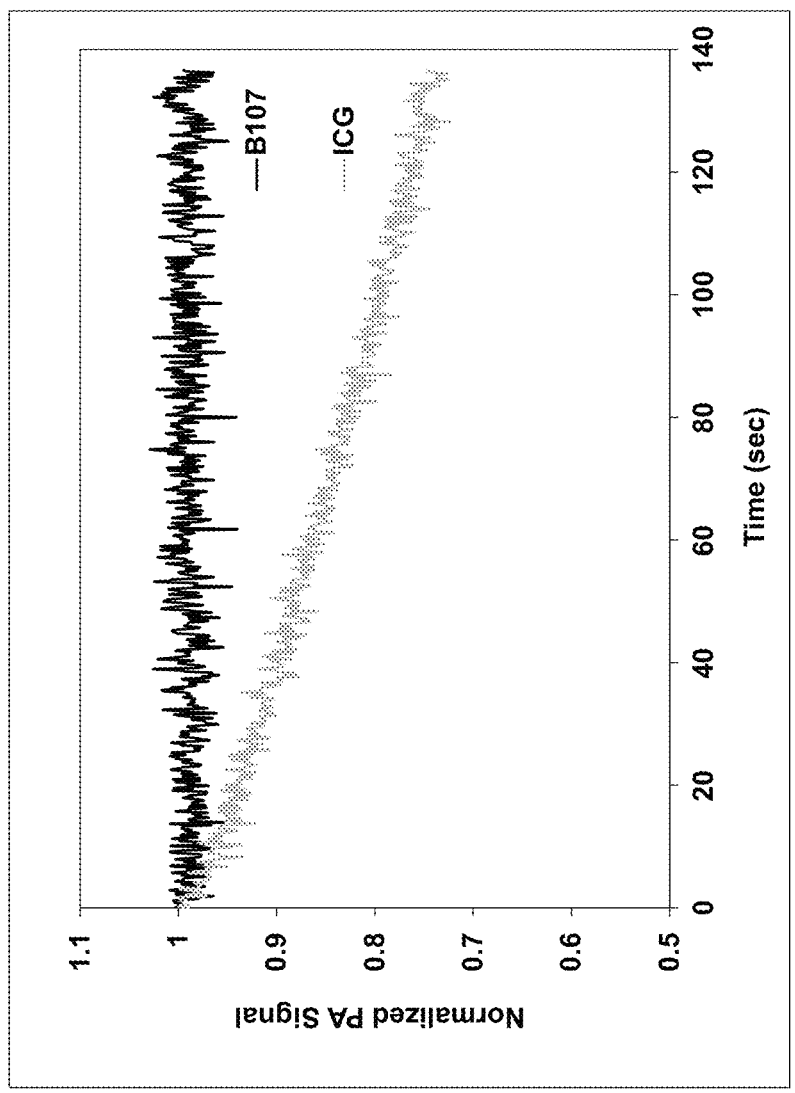
FIG. 4 is a plot comparing B107 (black) versus ICG (gray) PAI signal intensity over time with laser at 800 nm.

A third advantage and further benefit of nickel-bacteriochlorin complexes is their improved photostability. FIG. 4 shows the signals for ICG and the nickel-bacteriochlorin B107 in agar phantoms measured with continuous 800 nm laser illumination. It is possible the enhanced stability may be due to the limited conversion to an excited triplet state and subsequent limited degradation upon generation of singlet oxygen.

In sum, some benefits of employing bacteriochlorins and bacteriochlorin derivatives as PAI contrast agents include the following:

Tunable wavelengths and narrow emissions will enable multiplexing, Synthetic design is amenable to adding solubilizing groups and bioconjugatable tethers;

Greatly enhanced signal metallobacteriochlorins (M=Zn, Ni, Fe, Mn, Co, and/or Cu) will enable PAI detection of biomarkers at greater depths than conventional markers; and Enhanced probe stability will be useful for photoacoustic microscopy, image-guided surgery and other procedures requiring extended image acquisition times.

In addition to nickel chlorins and bacteriochlorins, in some embodiments the presently disclosed subject matter provides corresponding copper (Cu), iron (Fe), zinc (Zn), manganese (Mn), and/or cobalt (Co) metallochlorins and/or metallobacteriochlorins that provide enhancement of signal for PAI. In some embodiments, the complexed metal in the metallochlorin and/or metallobacteriochlorin is copper. In some embodiments, the complexed metal in the metallochlorin and/or metallobacteriochlorin is manganese.

The metallochlorins and/or metallobacteriochlorins can be used in some embodiments as contrast agents for general imaging of physiological features such as but not limited to organs, veins, lymph nodes, and lymph systems, and in some embodiments they can be used as targeted probes by attaching targeting agents. As used herein, the phrase "targeting agent" refers to any molecule that when attached to a composition of the presently disclosed subject matter enhances the accumulation of the composition in a target site such as, but not limited to a cell, a tissue, or an organ. For example, attachment of a metallochlorin and/or metallobacteriochlorin through a reactive linker or tether to an antibody can be accomplished by methods which have been previously established for free base chlorins and/or bacteriochlorins. In some embodiments, solubilizing groups such as carboxylates or PEG chains can improve the biolabeling efficiency and bioconjugate stability of a targeting composition of the presently disclosed subject matter (i.e., a metallochlorin, bacteriochlorin, or derivative thereof to which a targeting agent has been complexed). See e.g., Jiang et al., 2015; Zhang et al., 2016.

In some embodiments it can be preferred to incorporate a metallochlorin and/or metallobacteriochlorin into a nanoparticle, microbead, micelle, or other carrier structure to further enhance the PAI signal and/or to influence biodistribution. Exemplary methods for incorporating hydroporphyrins, including chlorins, bacteriochlorins, and derivatives thereof such as but not limited to metallochlorins, metallobacteriochlorins, and derivatives thereof in microbeads are disclosed, for example, in PCT International Patent Application Publication No. WO 2017/214637, the entire content of which is incorporated herein by reference. Other nanoparticles include liposomes and doped silica nanoparticles.

In addition to chlorins and/or bacteriochlorins and derivatives thereof, in some embodiments other hydroporphyrins such as but not limited to isobacteriochlorins and some chlorins with longer wavelength NIR absorptions are used for PAI panels.

Chlorins, metallochlorins, bacteriochlorins, metallobacteriochlorins, and their derivatives can in some embodiments be used in multi-color PAI panels as well as multi-modal multi-color panels for imaging or image-guided therapy (e.g., image-guided surgery or image-guided drug delivery). Multi-mode examples include fluorescence/PAI and MRI/PAI.

Figure 7:
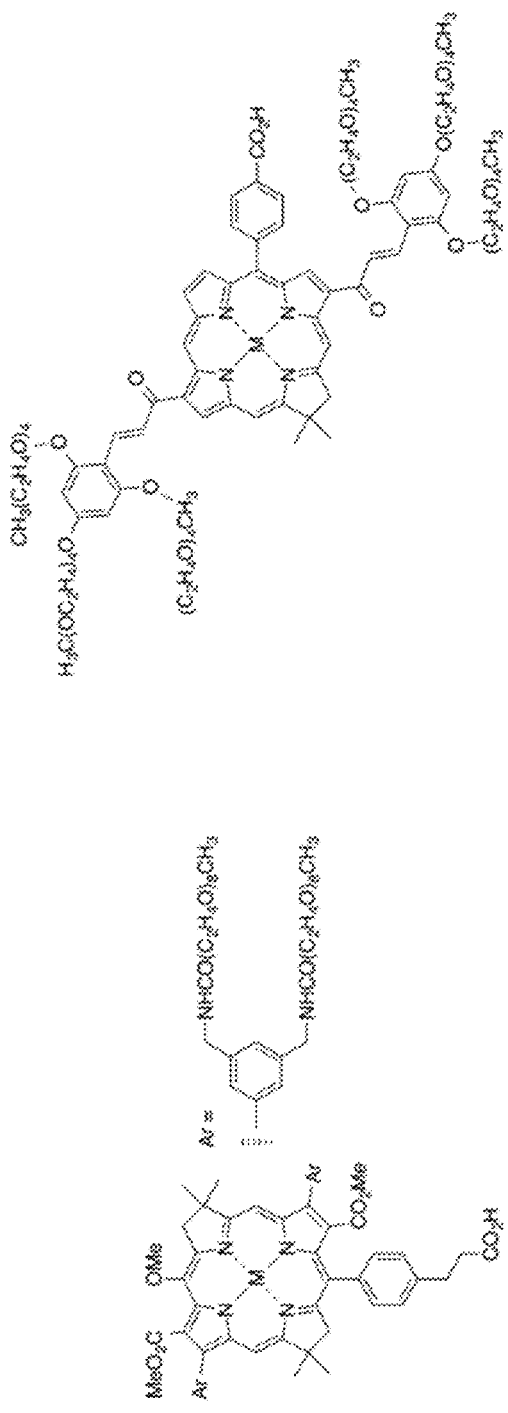
FIG. 7 shows examples of water soluble metallobacteriochlorins (left) and metallochlorins (right) with bioconjugatable tethers (M=Ni, Fe, Co). The carboxylates can be converted to a reactive ester for bioconjugation to amines on biomolecules (examples include N-hydroxy-succinimidyl, N-hydroxy-sulfo-succinimidyl, pentafluorophenyl, etc.) or to other groups such as iodoacetamide or maleimides for coupling to thiols on biomolecules.

Non-limiting examples of water-soluble metallobacteriochlorins and metallochlorins with tethers for bioconjugation are presented in FIG. 7.

This, the presently disclosed subject matter provides in some embodiments photoacoustic imaging (PAI) contrast agents. In some embodiments, the PAI contrast agents comprise at least one radiation-absorbing component that comprises a metallobacteriochlorin, a metallochlorin, a derivative thereof, or any combination thereof, wherein the metallobacteriochlorin, the metallochlorin, or the derivative thereof is complexed to copper and/or manganese. In some embodiments, the PAI contrast agent comprises a plurality of different copper-complexed and/or manganese-complexed bacteriochlorins, copper-complexed and/or manganese-complexed chlorins, derivatives thereof, or combinations thereof, wherein each copper-complexed and/or manganese-complexed bacteriochlorin, copper-complexed and/or manganese-complexed chlorin, or derivative thereof has a different absorption spectrum in the range of 650-1070 nm. In some embodiments, the photoacoustic imaging contrast agent comprises at least three different metallobacteriochlorins, metallochlorins, and/or derivatives thereof, wherein each metallobacteriochlorin, metallochlorin, and/or derivative thereof has an absorption spectrum with a peak absorption value in the range of 700-950 nm; and the at least three absorption spectra are substantially non-overlapping in the range of 700-950 nm. In some embodiments, the metallobacteriochlorin and/or metallochlorin comprises a metal selected from the group consisting of zinc, copper, nickel, iron, cobalt, manganese, and copper. In some embodiments, the metallobacteriochlorin and/or metallochlorin comprises copper and/or manganese. In some embodiments, the photoacoustic imaging contrast agent comprises at least one copper-complexed bacteriochlorin, copper-complexed chlorin, and/or derivative thereof, and at least one additional metallobacteriochlorin, metallochlorin, and/or derivative thereof complexed to a metal selected from the group consisting of zinc, nickel, iron, manganese, and cobalt.

In some embodiments, the presently disclosed subject matter also provides photoacoustic imaging contrast agents. In some embodiments a photoacoustic imaging contrast agent of the presently disclosed subject matter comprises at least one radiation-absorbing component comprising a bacteriochlorin, a metallobacteriochlorin, a derivative thereof, or a combination thereof. In some embodiments, the at least one radiation-absorbing component comprises a compound selected from the group consisting of:

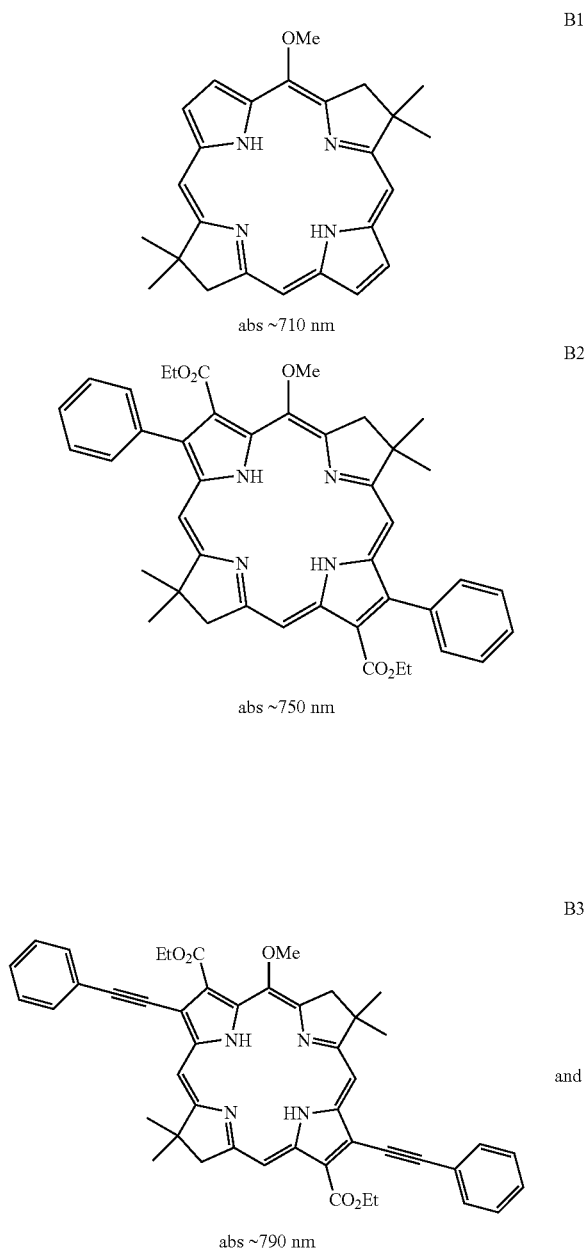

B107

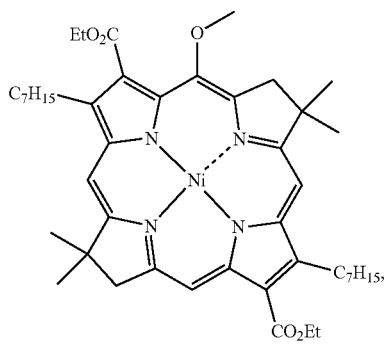

In some embodiments, the at least one radiation-absorbing component comprises a derivative of B1-B3 and B107 comprising a complexed metal, wherein the complexed metal is selected from the group consisting of zinc, copper, manganese, nickel, cobalt, and iron. In some embodiments, the complexed metal is copper and/or manganese. In some embodiments, the derivative comprises a compound selected from the group consisting of:

MB1

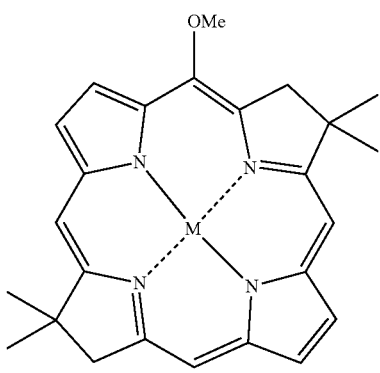

MB2

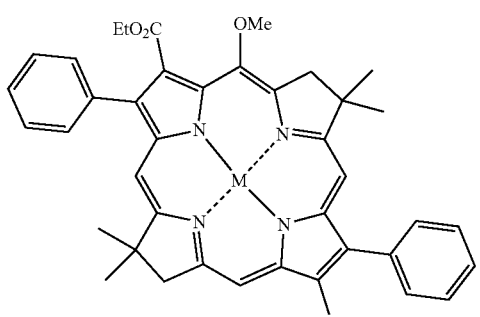

and

MB3

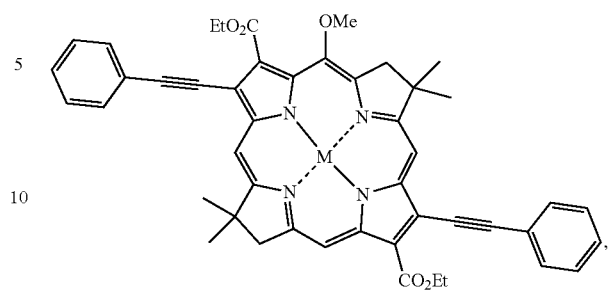

wherein M is a metal, optionally a metal selected from the group consisting of zinc, copper, manganese, nickel, cobalt, and iron. In some embodiments, the complexed metal is copper and/or manganese. In some embodiments, the at least one radiation-absorbing component comprises a compound selected from the group consisting of MBC-1, MBC-2, and MBC-3, wherein MBC-1, MBC-2, and MBC-3 have the following structures:

MBC-1

MBC-2

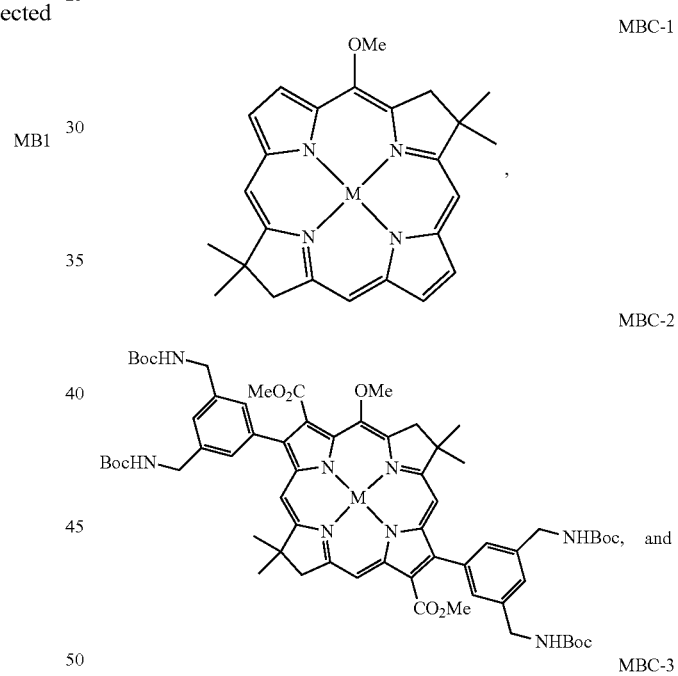

MBC-3

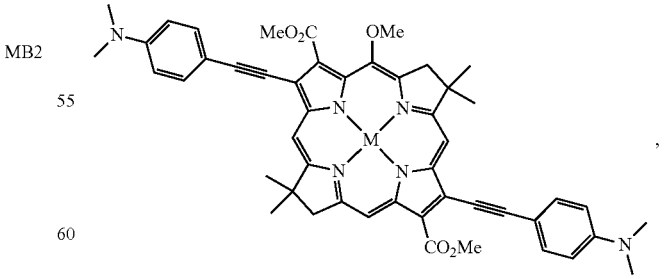

and further wherein M is a metal selected from the group consisting of zinc (Zn), nickel (Ni), iron (Fe), cobalt (Co), manganese (Mn) and copper (Cu). In some embodiments, the at least one radiation-absorbing component comprises CuBC-725, CuBC-775, or CuBC-840, wherein CuBC-725, CuBC-775, and CuBC-840 have the following structures:

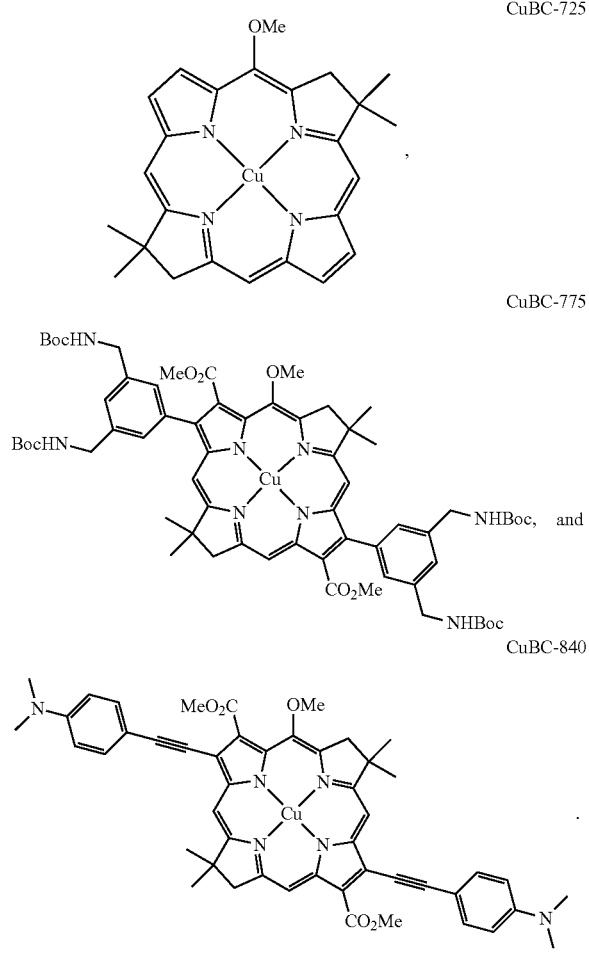

In some embodiments, the photoacoustic imaging contrast agent is physiologically tolerable for use in a subject, optionally a human.

In some embodiments, the presently disclosed subject matter provides pharmaceutical compositions. In some embodiments, the presently disclosed pharmaceutical compositions comprise one or more photoacoustic imaging contrast agents as described herein and a pharmaceutically acceptable carrier, diluent, or excipient. In some embodiments, the pharmaceutical composition is pharmaceutically acceptable for use in a human.

These and other aspects and embodiments which will be apparent to those of skill in the art upon reading the present disclosure, which provides the art with compositions and methods useful for detecting and/or labeling biological molecules and/or cells, particularly in the context of photoacoustic imaging and/or Multispectral Optoacoustic Tomography (MSOT).

III. Synthesis of Chlorins, Metallochlorins, Bacteriochlorins, Metallobacteriochlorins, and Derivatives Thereof The chlorins and bacteriochlorins that can serve as starting materials for synthesizing the radiation-absorbing molecules of the presently disclosed subject matter can be produced by any method known to those of skill in the art. Exemplary methods for synthesizing chlorins and bacteriochlorins and related molecules are disclosed in, for example, U.S. Pat. Nos. 6,559,374; 7,470,785; 7,534,807; 8,129,520; 8,173,691; 8,173,692; 8,207,329; 8,304,561; 8,664,260; 9,365,722; and 9,822,123; and in PCT International Patent Application Publication No. WO 2017/214637, the content of each of which is hereby incorporated by reference in its entirety. Particular exemplary methods for synthesizing bacteriochlorins and related molecules are as follows.

In some embodiments, a method for synthesizing a bacteriochlorin of the presently disclosed subject matter comprises condensing a pair of compounds of Formula IIA:

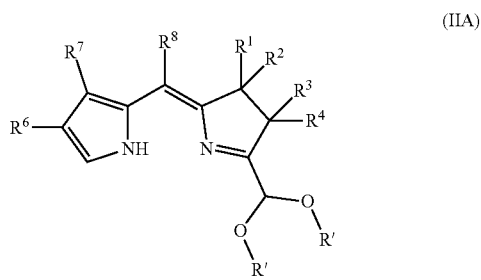

(IIA)

in an organic solvent in the presence of an acid, where each R' independently represents C1-C4 alkyl, or both R' together represent C2-C4 alkylene; to produce a compound of Formula I wherein $R^5$ is H or alkoxy;

when $R^5$ is H, optionally brominating, and then optionally further substituting the compound at the $R^5$ position; to produce Formula IA, wherein Formula IA is:

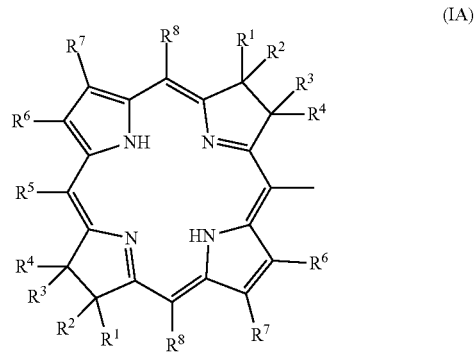

(IA)

wherein:
each $R^1$, $R^2$, $R^3$, $R^4$, $R^5$, $R^6$, $R^7$ and $R^8$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups;

or $R^1$ and $R^2$ together are =O or spiroalkyl;

or $R^3$ and $R^4$ together are =O or spiroalkyl;

or where $R^6$ and $R^7$, or $R^7$ and $R^8$, together represent a fused aromatic or heteroaromatic ring systems. In some embodiments, the compound of Formula I can then be metalated, including but not limited to metalated with copper, as desired. In some embodiments, each of $R^3$ and $R^4$ are methyl.

Alternatively, a method for synthesizing a bacteriochlorin of the presently disclosed subject matter can include condensing a compound of Formula IIB and a compound of Formula III in a composition comprising a first solvent to produce an intermediate;

wherein the compound of Formula IIB has a structure represented by:

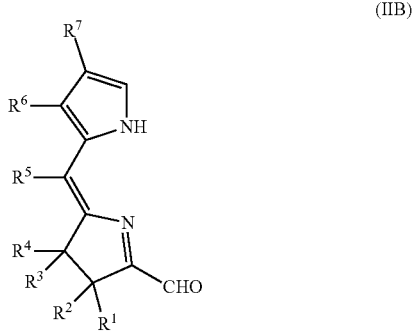

(IIB)

wherein $R^1$, $R^2$, $R^3$, $R^4$, $R^5$, $R^6$, and $R^7$ are as provided below;

wherein the compound of Formula III has a structure represented by:

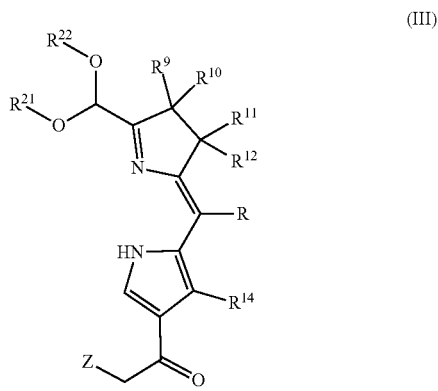

(III)

wherein $R^9$, $R^{10}$, $R^{11}$, $R^{12}$, $R^{13}$, and $R^{14}$ are as provided below; and $R^{21}$ and $R^{22}$ are each independently selected from the group consisting of hydrogen, alkyl and aryl, or $R^{21}$ and $R^{22}$ taken together represent a C2-C4 alkylene; and condensing the intermediate in a second solvent in the presence of an acid to produce the compound of Formula IV or a metal conjugate thereof, wherein Formula IV is defined as:

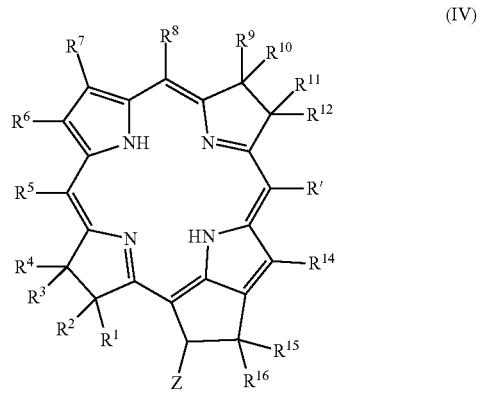

(IV)

or a metal conjugate thereof (e.g., a copper chelate thereof), wherein:

$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups;

or $R^1$ and $R^2$ together are =O or spiroalkyl;

or $R^3$ and $R^4$ together are =O or spiroalkyl;

or each $R^3$ and $R^4$ is methyl;

or $R^9$ and $R^{10}$ together are =O or spiroalkyl;

or $R^{11}$ and $R^{12}$ together are =O or spiroalkyl;

or $R^{15}$ and $R^{16}$ together are =O;

or $R^5$ and $R^6$ together represent a fused aromatic or heteroaromatic ring systems;

or $R^6$ and $R^7$ together represent a fused aromatic or heteroaromatic ring systems;

or $R^{13}$ and $R^{14}$ together represent a fused aromatic or heteroaromatic ring systems; and Z is an electron-withdrawing group (e.g., —CO$_2$R$^{17}$, —C(O)NHR$^{17}$, —C(O)NR$^{17}$R$^{18}$, —C(O)R$^{17}$, —CN, —C=N—NR$^{17}$R$^{18}$, —PO(OR$^{17}$)$_2$, —SO$_2$OR$^{17}$, —SO$_2$NR$^{17}$R$^{18}$, —SO$_2$R$^{17}$, and —SiR$^{17}$R$^{18}$R$^{19}$, and wherein R$^{17}$, R$^{18}$, and R$^{19}$ are, in each occurrence, independently selected from the group consisting of hydrogen, alkyl and aryl).

Additional exemplary routes to synthesis of bacteriochlorins include the Northern-Southern Route described in Liu & Lindsey, 2016 and the methods for synthesizing bacteriochlorin macrocycles with annulated isocyclic rings described in Zhang & Lindsey, 2017, the content of each of which is incorporated herein by reference in its entirety.

Figure 5:
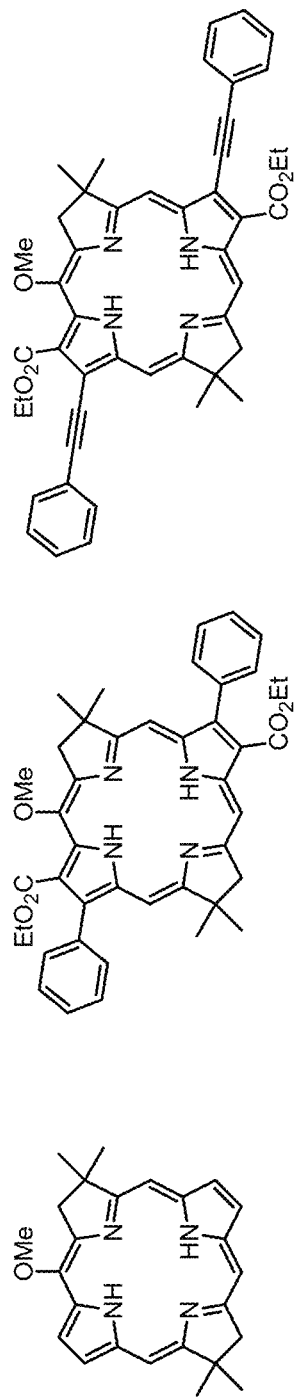
FIG. 5 shows the structures of three bacteriochlorins (bacteriochlorins B1-B3) with spectrally distinct absorption bands. Representative absorption spectra for bacteriochlorins B1-B3 are depicted in FIG. 1.
Figure 6:
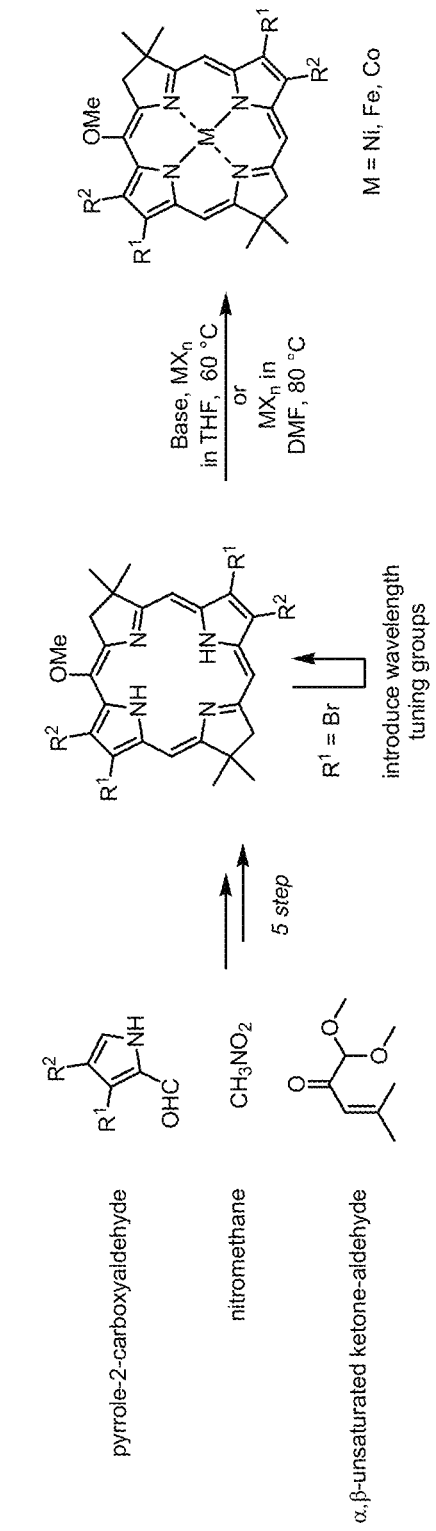
FIG. 6 depicts an exemplary non-limiting synthesis scheme for bacteriochlorins (B1: $R^1=R^2=H$; B2: $R^1$=Phenyl, $R^2=CO_2Me$; B3: $R^1$=Br and then is converted to phenylethynyl groups through Sonogashira coupling at latter stage, $R^2=CO_2Me$).
Figure 8:
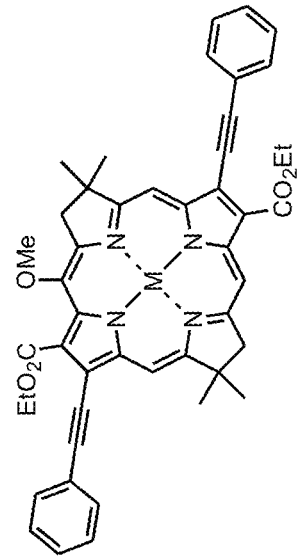
FIG. 8 shows the structures of three exemplary metallobacteriochlorins (metallobacteriochlorins MB1-MB3), where M is a metal, optionally a metal selected from the group consisting of zinc (Zn), copper (Cu), nickel (Ni), cobalt (Co), manganese (Mn) and iron (Fe). In some embodiments, the complexed metal is copper (Cu).
Figure 8:
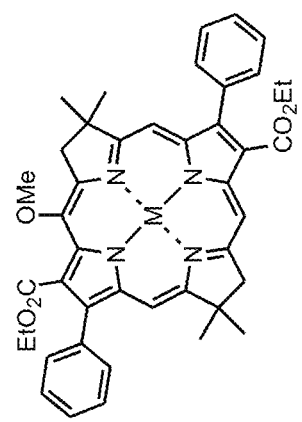
Figure 8:
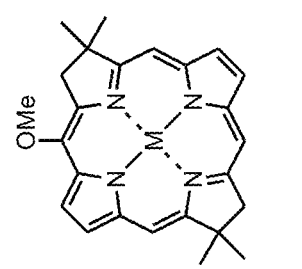

Three exemplary bacteriochlorins that can be employed in a bacteriochlorin panel (e.g., bacteriochlorins B1-B3) are shown in FIG. 5. These can be converted to the corresponding metallobacteriochlorins (depicted in FIG. 8) which would be expected to have a similar spread of peak signal in PAI with low overlap between them and a 20-30 nm shift in peak spectral wavelengths from the free base bacteriochlorins. FIG. 6 is a brief outline of methods of synthesis of bacteriochlorins B1-B3. Bacteriochlorins B1 and B2 can be synthesized by known methods (see Krayer et al., 2010) in five steps, starting from the corresponding pyrole-2-carboxaldehyde. Bacteriochlorin B3 requires the bromo-substituted bacteriochlorin ($R^1$=Br) undergoing Sonogashira coupling to install the phenylethynyl groups to achieve the desired absorption at ~790 nm. An analogue of bacteriochlorin B3 has been synthesized and was verified to meet this wavelength expectation.

Metallochlorins exhibit similar photoacoustic signals to metallobacteriochlorins, typically at shorter wavelengths. Synthetic methods for preparing metallochlorins typically also involve addition of a metal salt in the presence of base, typically during the final ring closure reaction of a tetrahydrbiladiene precursor to form the metallochlorin. Such methods are described in detail by Ptaszek et al., 2007, which is incorporated herein by reference in its entirety.

Metalation of each chlorin and/or bacteriochlorin can be achieved by recently developed methods as essentially described in Chen et al., 2012. The metalation of synthetic chlorins and/or bacteriochlorins was advanced to cover the synthetic chlorins and/or bacteriochlorins bearing various substitution patterns, ranging from electron-withdrawing to electron-rich functions. In general, two methods can be utilized in the metalation depending on the nature of the chlorins and/or bacteriochlorins. The electron-rich chlorins and/or bacteriochlorins can be metalated by treating with strong bases (NaH or LDA) in THF, following by addition of metal salts ($MX_n$) at 60° C. The electron-deficient bacteriochlorins can be metalated by treating with metal salts ($MX_n$) in DMF at elevated temperature. The two methods have been previously used to prepare various synthetic Zn—, Cu—, Pd— and Ni-bacteriochlorins. These methods can also be employed for synthetic Mn—, Fe—, and Co-bacteriochlorins via metalation of free-base bacteriochlorins with Mn, Fe and Co. By way of example and not limitation, syntheses of Mn-bacteriochlorins by related methods is described by Schaberle et al (2017).

Figure 9A:
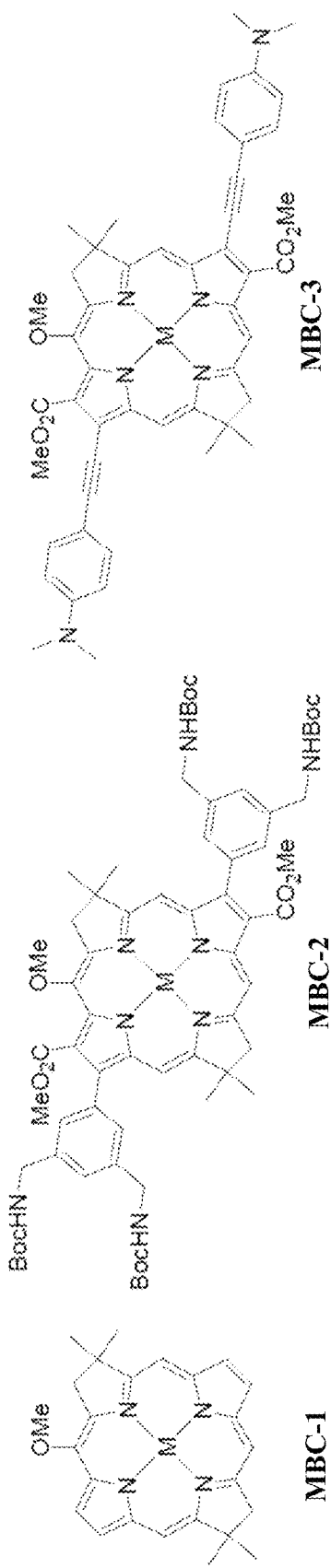
FIGS. 9A and 9B show the structures of three additional exemplary metallobacteriochlorins (metallobacteriochlorins MBC-1, MBC-2, and MBC-3; see FIG. 9A), where M is a metal, optionally a metal selected from the group consisting of zinc (Zn), copper (Cu), nickel (Ni), cobalt (Co), manganese (Mn) and iron (Fe). In some embodiments, the complexed metal is copper (Cu).
Figure 9B:
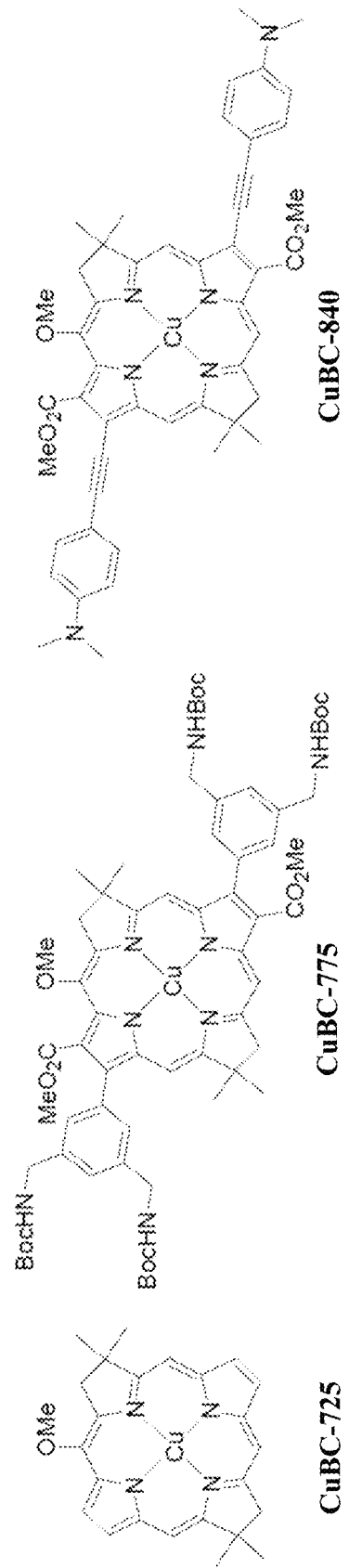

Three additional exemplary bacteriochlorins that can be employed in a bacteriochlorin panel (e.g., bacteriochlorins MBC-1, MBC-2, and MBC-3) are shown in FIG. 9A. These can be converted to the corresponding metallobacteriochlorins (examples of which are depicted in FIG. 9B) which would be expected to have a similar spread of peak signal in PAI with low overlap between them and a 20-30 nm shift in peak spectral wavelengths from the free base bacteriochlorins.

IV. Methods of PAI Using the Compositions of the Presently Disclosed Subject Matter Photoacoustic imaging is a technique wherein non-ionizing laser pulses are delivered to biological tissues. A fraction of the delivered energy is absorbed and converted into heat, leading to transient thermoelastic expansion and ultrasonic emission. The generated ultrasonic waves are thereafter detected and analyzed to produce images of the biological tissues. Generally, the magnitude of the ultrasonic emission reveals physiologically specific optical absorption contrast. 2D or 3D images of the targeted areas can then be formed. See e.g., U.S. Patent Application Publication Nos. 2005/0085725; 2009/0066949; 2009/0069653; 2010/0226003; and 2012/0296192; U.S. Pat. Nos. 6,738,653; 7,864,307; 7,916,283; PCT International Patent Application Publication No. WO 2002/008740; and Xu & Wang, 2006; Li & Wang, 2009; Li et al., 2009; Wang, 2009; Yang et al., 2009; each of which is incorporated herein by reference in its entirety.

As such, in some embodiments the presently disclosed subject matter provides methods for generating an image of a volume. In some embodiments, the methods comprise administering to the volume or the part thereof a contrast agent comprising at least one radiation-absorbing component comprising a metallobacteriochlorin, a metallochlorin, or a derivative thereof, wherein the metallobacteriochlorin, the metallochlorin, and/or the derivative thereof is complexed to copper and/or manganese; exposing the volume or the part thereof to radiation; detecting ultrasonic waves generated in the volume or the part thereof by the radiation; and generating a photoacoustic image therefrom of the volume or the part thereof containing the administered contrast agent. In some embodiments, the metallobacteriochlorin, the metallochlorin, and/or the derivative thereof is a component of and/or encapsulated in a micelle, a liposome, a nanoparticle, or a combination thereof. In some embodiments, radiation with a wavelength of 650-1070 nm is used. In some embodiments, radiation with a wavelength of 650-900 nm, 700-950 nm, and/or 750-950 nm is used. In some embodiments, the physiologically tolerable contrast agent comprises a plurality of different metallobacteriochlorins, metallochlorins, derivatives thereof, and/or combinations thereof, each metallobacteriochlorin, metallochlorin, and/or the derivative thereof having a different absorption spectrum in the range of 650-1070 nm. In some embodiments, the contrast agent comprises a targeting agent. In some embodiments, the targeting agent comprises a moiety that binds to a ligand and/or a target present on a tumor cell or a cancer cell, or a vascular endothelial cell associated therewith. In some embodiments, the ligand and/or a target comprises a tumor-associated antigen. In some embodiments, the moiety comprises a peptide or peptide mimetic that binds to a tumor-associated antigen.

The presently disclosed subject matter also provides in some embodiments methods for multiplex photoacoustic imaging of a volume. In some embodiments, the methods comprise administering to the volume or the part thereof a contrast agent comprising a plurality of radiation-absorbing components, each member of the plurality of radiation-absorbing components comprising a metallobacteriochlorin, a metallochlorin, and/or a derivative thereof, wherein the metallobacteriochlorin, the metallochlorin, and/or the derivative thereof is complexed to copper and/or manganese; exposing the volume or a part thereof to radiation, wherein the radiation is calibrated to wavelengths that are differentially absorbed by the plurality of radiation-absorbing components; differentially detecting ultrasonic waves generated in the volume or the part thereof by the radiation as it is differentially absorbed by the plurality of radiation-absorbing components; and generating a photoacoustic image therefrom of the volume or the part thereof containing the administered contrast agent, wherein the photoacoustic image is generated from the differentially detecting ultrasonic waves. In some embodiments, one or more of the plurality of the metallobacteriochlorins, the metallochlorins, and/or the derivatives thereof is a component of and/or encapsulated in a micelle, a liposome, a nanoparticle, or a combination thereof. In some embodiments, radiation with a wavelength of 650-1070 nm is used. In some embodiments, radiation with a wavelength of 650-900 nm, 700-950 nm, and/or 750-950 nm is used. In some embodiments, each member of the plurality of radiation-absorbing components has a different absorption spectrum in the range of 650-1070 nm. In some embodiments, one or more of the members of the plurality of radiation-absorbing components comprises a targeting agent. In some embodiments, the targeting agent comprises a moiety that binds to a ligand and/or a target present on a tumor cell or a cancer cell, or a vascular endothelial cell associated therewith. In some embodiments, the ligand and/or a target comprises a tumor-associated antigen. In some embodiments, the moiety comprises a peptide or peptide mimetic that binds to a tumor-associated antigen. In some embodiments, two or more of the members of the plurality of radiation-absorbing components comprise a targeting agent. In some embodiments, the two or more of the members of the plurality of radiation-absorbing components comprise different targeting agents. In some embodiments, the different targeting agents bind to and/or otherwise accumulate in the same or different targets and/or targeted sites.

Furthermore, in some embodiments of the methods of the presently disclosed subject matter, the volume is a subject or a body part thereof, optionally a cell, tissue, and/or organ thereof. In some embodiments, the volume comprises a tumor cell, a cancer cell, or a tumor or cancer-associated vascular cell. In some embodiments, the contrast agent is a physiologically tolerable contrast agent or a plurality of physiologically tolerable contrast agents. In some embodiments, the contrast agent is physiologically tolerable for use in a human. In some embodiments, the contrast agent is provided in a pharmaceutical composition comprising the photoacoustic imaging contrast agent and a pharmaceutically acceptable carrier, diluent, or excipient. In some embodiments, the pharmaceutical composition is pharmaceutically acceptable for use in a human. In some embodiments, the volume comprises one or more targets and/or targeted sites that can be targeted by a targeting agent.

Thus, the presently disclosed methods can be employed in in vivo, ex vivo, and in vitro uses. When employed in vivo, the presently disclosed methods can employ contrast agents that are physiologically tolerable for use in a subject, optionally a human. In some embodiments, the contrast agents are formulated as part of a pharmaceutical composition, which in some embodiments can further comprise one or more pharmaceutically acceptable carriers, diluents, and/or excipient. In some embodiments, the pharmaceutical composition is pharmaceutically acceptable for use in a human. Suitable formulations include aqueous and non-aqueous sterile injection solutions which can contain anti-oxidants, buffers, bacteriostats, bactericidal antibiotics, and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are sodium dodecyl sulfate (SDS) in the range of in some embodiments 0.1 to 10 mg/ml, in some embodiments about 2.0 mg/ml; and/or mannitol or another sugar in the range of in some embodiments 10 to 100 mg/ml, in some embodiments about 30 mg/ml; and/or phosphate-buffered saline (PBS). Any other agents conventional in the art having regard to the type of formulation in question can be used.

In some embodiments, the presently disclosed compositions are employed as contrast agents and/or as components of multi-color PAI panels and/or multi-modal multi-color panels for imaging or image-guided therapy (see e.g., U.S. Pat. No. 8,617,522; incorporated herein by reference).

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Materials and Methods Used in the Examples

Indocyanine Green (ICG), was obtained from Sigma-Aldrich (Catalogue No. 12633; Sigma-Aldrich Corp., St. Louis, Mo., United States of America). The nickel bacteriochlorin B107 was prepared as described in Sun et al., 2013 and Chen et al, 2012. Each dye was dissolved in N,N-dimethylformamide (DMF) at the desired concentrations prior to the imaging experiments. Molds for preparing agar phantoms were typically 90 mm diameter glass Petri dishes.

Example 1

Phantom Preparation

A highly purified agar powder (Catalogue No. A7921; Sigma-Aldrich Corp., St. Louis, Mo., United States of America) was dissolved in water (Reagent Grade, Type I) to a final concentration of 2.0% and heated to the melting temperature of 95° C. in a microwave oven. Three 30 second cycles of heating and swirling to mix resulted in a smooth agar preparation. The bottle containing agar was held at 75-85° C. for 1-3 hours using a standard hot plate and a double boiler to avoid scorching (which causes a detectable increase in the absorption coefficient). This waiting period at an elevated temperature allows the slow release of air bubbles and produces an agar solution with negligible absorption and very low turbidity. The desired optical properties of the phantom were reached by adding a 20% (1:5 v/v) final concentration of 1.0% low fat milk as a scattering medium and India ink (Higgins Black 44201; Chartpak, Inc., Leeds, Mass., United States of America) as an absorbing medium. These additions were made in the range of 54-58° C. to avoid precipitation of the milk proteins. The solution was stirred slowly and continuously with a stir bar at a speed to maintain homogeneity of the milk and ink, but not cause bubbles or foaming.

Petri dishes were pre-warmed on a 50° C. hot plate for 1 minute prior to the dispensing of the Phantom matrix The phantom matrix solution was dispensed into the molds using a pre-warmed 25 ml serological pipette and left undisturbed to reach proper hardening and stable optical properties (20-25° C.). If the formed Phantoms were not used within four hours, they were sealed to limit evaporation. In general, the formed Phantoms were used within 8 hours or within 72 hours if stored refrigerated. If refrigerated, they were warmed to ambient temperature prior to use. This allows the phantom matrix to spread evenly prior to hardening allowing for optical flatness of the phantom surface (quickly aspirated and dispensed two times in the 50-53° C. Phantom matrix). Typically, 20 ml of the phantom matrix was added to obtain 3±10% mm thick molds. The 3 mm thick phantoms were stacked as needed in order to measure the PAI signal from dyes in polyethylene tubing extended across and under the agar layers at the desired depth.

Example 2

Photoacoustic Imaging of Agar Phantoms and Dyes

Photoacoustic imaging was performed using a VEVO® LAZR 2100 imaging system (VisualSonics, Inc., Toronto, Ontario, Canada) equipped with software version 1.7.2. This instrument combines Ultrasound with Photoacoustics Mode (PA) imaging and employs an optical parametric oscillator laser (OPO) pumped by a doubled Nd:YAG tunable laser. Imaging was performed in PA scanning mode (680-900 nm) with a 5 nm step size or at fixed wavelengths for a designated period of time. Dyes were introduced via syringe into PE50 polyethylene tubing (0.023"×0.038"; Braintree Scientific, Braintree, Mass., United States of America) and clamped at each end during the imaging experiments. Ultrasound gel was applied to the surface of the agar phantoms to ensure efficient coupling between the transducer and the Phantoms. The tubing and its associated image regions were isolated by ultrasound and PA signals for PA intensity quantitation. The data presented in FIGS. 3 and 4 were for solutions of 63 μM Ni-bacteriochlorin (B107) and 50 μM ICG, and indicated an approximately 5-fold greater signal for the Ni-bacteriochlorin at two depths of agar compared to ICG.

Example 3

Preparation of Other Metallobacteriochlorins, and Photoacoustic Imaging of Agar Phantoms and Dyes Using the Same Cobalt- (Co) and Iron- (Fe) bacteriochlorins that correspond to Ni-bacteriochlorin B107 are also prepared using the basic scheme depicted in FIG. 6. Additionally, Ni—, Co—, and Fe-bacteriochlorins that correspond to bacteriochlorins B1-B3 are also prepared using the basic scheme depicted in FIG. 6. Exemplary metalated bacteriochlorins are presented in FIG. 8.

Photoacoustic imaging of agar phantoms and dyes using the Co— and Fe-bacteriochlorin derivatives of B107 and the Ni—, Co—, and Fe-bacteriochlorin derivatives of bacteriochlorins B1-B3 are performed essentially as set forth in EXAMPLE 2. The intensities of the various signals and the normalized signals are compared to each other and to those of ICG.

Example 4

Preparation of Copper-Complexed Metallobacteriochlorins, and Photoacoustic Imaging of Agar Phantoms and Dyes Using the Same Three Copper Bacteriochlorins (CuBC-725, CuBC-775, and CuBC-840) were used to prepare PAI contrast agents (peak absorptions at 725, 775, and 840 nm, respectively) and ICG diluted in Dimethylformamide (DMF). The three contrast dyes were placed in straws and imaged in a 4-well agar scattering phantom next to control tubes filled with either DMF or ICG as described herein. Dilutions of 20 μM, 5 μM, and 1 μM were prepared. A full absorption spectrum was collected for each sample. Samples with two mixed dyes (CuBC-725/CuBC-775, CuBC-725/CuBC-840, and CuBC-775/CuBC-840) were also assayed. Convolved MSOT absorption spectra were evaluated using a MSOT inVision 512-Echo (iThera Medical GmbH, Munich, Germany) at imaging wavelengths ranging from 680 to 980 nm. ROI analysis was performed on reconstructed images at all recorded wavelengths to obtain the OA spectra. ROIs were drawn around the sample & control tubes. The spectra were measured at 3 Z-slices and averaged to increase SNR.

The results are presented in FIG. 10. As shown in FIG. 10, as compared ICG, each of CuBC-725, CuBC-775, and CuBC-840 was characterized by a sharper peak and increased absorption maximum.

REFERENCES

All references listed below, as well as all references cited in the instant disclosure, including but not limited to all patents, patent applications and publications thereof, scientific journal articles, and database entries are incorporated herein by reference in their entireties to the extent that they supplement, explain, provide a background for, or teach methodology, techniques, and/or compositions employed herein.

Abuteen et al. (2013) The evaluation of NIR-absorbing porphyrin derivatives as contrast agents in photoacoustic imaging. Phys Chem Chem Phys 15:18502-18509.

Bell (1880) Upon the production and reproduction of sound by light. Am J Sci 20:305-324. Chen et al. (2012) Synthesis and Physicochemical Properties of Metallobacteriochlorins Inorg Chem 51:9443-9464.

de Zerda et al. (2012) Family of Enhanced Photoacoustic Imaging Agents for High Sensitivity and Multiplexing Studies in Living Mice. ACS Nano 6:4694-4701.

Jiang et al. (2015) Polarity-tunable and wavelength-tunable bacteriochlorins bearing a single carboxylic acid or NHS ester. Use in a protein bioconjugation model system. New J Chem 39:403-419.

Krayer et al. (2010) Expanded Scope of Synthetic Bacteriochlorins via Improved Acid Catalysis Conditions and Diverse Dihydrodipyrrin-Acetals J Org Chem 75:1016-1039.

Landsman et al. (1976) Light-absorbing properties, stability, and spectral stabilization of indocyanine green, J Appl Physiol 40:575-583 (n.b. Data from this paper was obtained from: "Optical Absorption of Indocyanine Green (ICG)" S Prahl, Oregon Medical Laser Center [[http://]] omlc.org/spectra/icg/).

Li & Wang (2009) Photoacoustic tomography and sensing in biomedicine. Phys Med Biol 54:R59-R97.

Li et al. (2009) In-vivo photoacoustic microscopy of nanoshell extravasation from solid tumor vasculature. J Biomed Opt 14:010507.

Liu & Lindsey (2016) Northern-Southern Route to Synthetic Bacteriochlorins. J Org Chem 81:11882-11897.

Marshall et al. (2010) Single-Dose Intravenous Toxicity Study of IRDye 800CW in Sprague-Dawley Rats. Mol Imaging Biol 12:583-594

PCT International Patent Application Publication Nos. WO 2002/008740; WO 2017/214637.

Pilch et al. (2013) Molecular symmetry determines the mechanism of a very efficient ultrafast excitation-to-heat conversion in Ni-substituted chlorophylls. Biochimica et Biophysica Acta 1827:30-37.

Pitner et al. (2016) Chlorins: A novel family of violet laser-excitable red to far-red fluorophores for polychromatic flow cytometry. CYTO 2016, No. 318, June 2016.

Ptaszek et al (2007) Sparsely substituted chlorins as core constructs in chlorophyll analogue chemistry. I. Synthesis. Tetrahedron 63:3826-3839.

Schaberle et al. (2017) Ultrafast Dynamics of Manganese (III), Manganese (II), and Free-Base Bacteriochlorin: Is There Time for Photochemistry? Inorg Chem 56:2677-2689

Sun et al. (2013) Synthesis and Characterization of Lipophilic, Near-Infrared Absorbing Metallobacteriochlorins Chem J Chin Univ 34:776-781.

Taniguchi et al. (2008) Accessing the near-infrared spectral region with stable, synthetic, wavelength-tunable bacteriochlorins. New J Chem 32:947-958.

U.S. Patent Application Publication Nos. 2005/0085725; 2009/0066949; 2009/0069653; 2010/0226003; 2012/0296192.

U.S. Pat. Nos. 6,559,374; 6,738,653; 7,470,785; 7,534,807; 7,864,307; 7,916,283; 8,129,520; 8,173,691; 8,173,692; 8,207,329; 8,304,561; 8,617,522; 8,664,260; 9,365,722; 9,822,123.

Xu & Wang (2006) Photoacoustic Imaging in Biomedicine. Rev Sci Instrum 77:041101 (DOI: [[http://]]dx.doi.org/10.1063/1.2195024).

Wang (2009) Multiscale photoacoustic microscopy and computed tomography. Nature Photonics 3:503-509.

Wang & Yao (2016) A practical guide to photoacoustic tomography in the life sciences. Nature Methods 13:627-638.

Wilson et al. (2013) Acoustic and Photoacoustic Molecular Imaging of Cancer. J Nucl Med 54:1851-1854.

Yang et al. (2009) Nanoparticles for photoacoustic imaging. Wiley Interdiscip Rev Nanomed Nanobiotechnol 1:360-368.

Zhang & Lindsey (2017) Construction of the Bacteriochlorin Macrocycle with Concomitant Nazarov Cyclization To Form the Annulated Isocyclic Ring: Analogues of Bacteriochlorophyll a. J Org Chem 82:2489-2504.

Zhang et al. (2016) Bioconjugatable, PEGylated Hydroporphyrins for Photochemistry and Photomedicine. Narrow-Band, Near-Infrared-Emitting Bacteriochlorins. New J Chem 40:7750-7767.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A photoacoustic imaging contrast agent comprising at least one radiation-absorbing component, wherein the at least one radiation-absorbing component comprises a metallobacteriochlorin selected from the group consisting of MBC-1, MBC-2, and MBC-3, wherein MBC-1, MBC-2, and MBC-3 have the following structures:

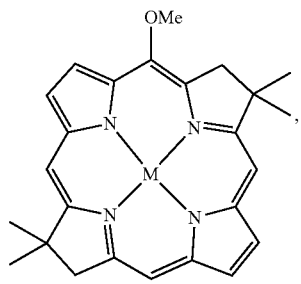

MBC-1

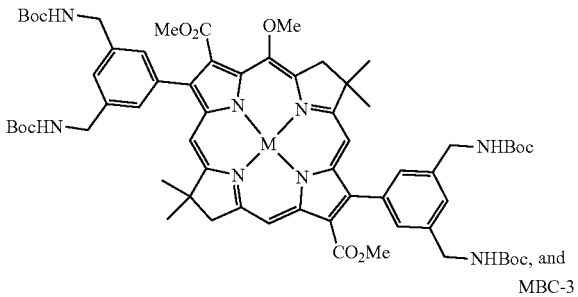

MBC-2

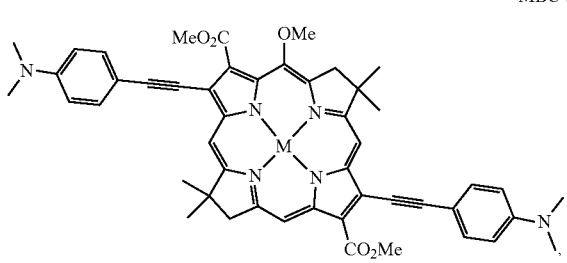

MBC-3 further wherein M is selected from the group consisting of copper and manganese.

2. The photoacoustic imaging contrast agent of claim 1, comprising a plurality of different metallobacteriochlorins, metallochlorins, or combinations thereof, at least one of which comprises a radiation-absorbing component selected from the group consisting of MBC-1, MBC-2, and MBC-3, wherein M is selected from the group consisting of copper and manganese, and further wherein each metallobacteriochlorin or metallochlorin has a different absorption spectrum in the range of 650-1070 nm and is complexed to copper, manganese, zinc, nickel, iron, or cobalt.

3. The photoacoustic imaging contrast agent of claim 2, wherein:

(i) the photoacoustic imaging contrast agent comprises at least three different metallobacteriochlorins or metallochlorins, at least one of which comprises a radiation-absorbing component selected from the group consisting of MBC-1, MBC-2, and MBC-3, wherein M is selected from the group consisting of copper and manganese;

(ii) each metallobacteriochlorin or metallochlorin has an absorption spectrum with a peak absorption value in the range of 700-950 nm; and (iii) the at least three absorption spectra are substantially non-overlapping in the range of 700-950 nm.

4. The photoacoustic imaging contrast agent of claim 3, wherein the photoacoustic imaging contrast agent comprises at least one copper-complexed bacteriochlorin and/or copper-complexed chlorin, and at least one additional metallobacteriochlorin or metallochlorin complexed to a metal selected from the group consisting of manganese, zinc, nickel, iron, and cobalt.

5. The photoacoustic imaging contrast agent of claim 1, wherein the at least one radiation-absorbing component comprises CuBC-725, CuBC-775, or CuBC-840, wherein CuBC-725, CuBC-775, and CuBC-840 have the following structures:

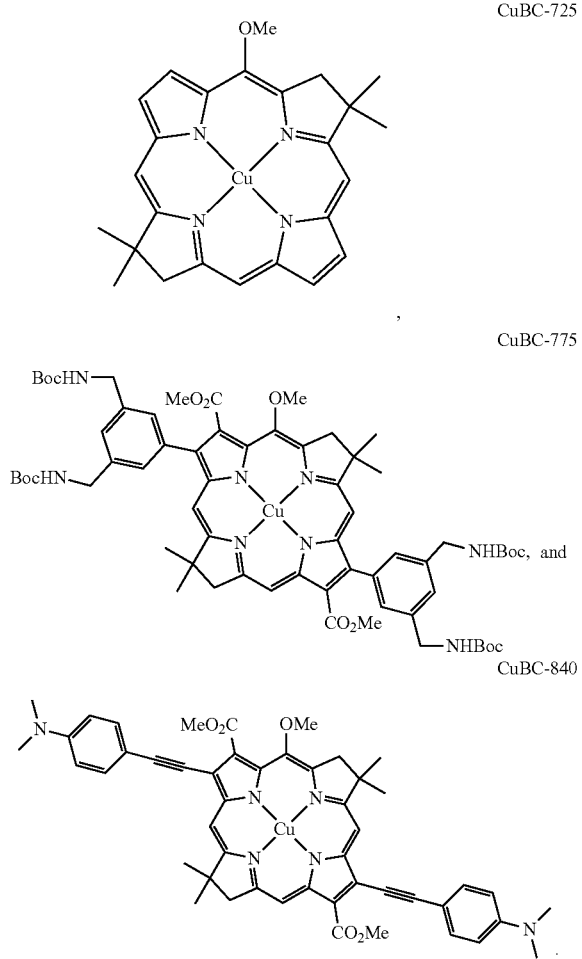

6. A pharmaceutical composition comprising the photoacoustic image contrast agent of claim 1 and a pharmaceutically acceptable carrier, diluent, or excipient, optionally wherein the pharmaceutical composition is pharmaceutically acceptable for use in a human.

7. A method of generating an image of a volume, the method comprising:
   (a) contacting the volume with at least one photoacoustic imaging contrast agent of claim 1;
   (b) exposing the volume to radiation;
   (c) detecting ultrasonic waves generated in the volume by the radiation; and
   (d) generating a photoacoustic image therefrom of the volume or part thereof containing the contrast agent.

8. The method of claim 7, wherein the metallobacteriochlorin or the metallochlorin is a component of and/or encapsulated in a micelle, a liposome, a nanoparticle, or a combination thereof.

9. The method of claim 7, wherein the volume is exposed to radiation with a wavelength of 650-900 nm, 700-950 nm, and/or 750-950 nm.

10. The method of claim 7, wherein the contrast agent comprises a plurality of different metallobacteriochlorins, metallochlorins and/or combinations thereof, each metallobacteriochlorin or metallochlorin having a different absorption spectrum in the range of 650-1070 nm.

11. The method of claim 7, wherein the contrast agent comprises a targeting agent.

12. The method of claim 11, wherein the targeting agent comprises a moiety that binds to a ligand and/or a target present on a tumor cell or a cancer cell, or a vascular endothelial cell associated therewith.

13. The method of claim 12, wherein the ligand and/or a target comprises a tumor-associated antigen.

14. The method of claim 7, wherein the volume is a subject or a body part thereof, optionally a cell, tissue, and/or organ thereof, further optionally a tumor cell, a cancer cell, or a tumor- or cancer-associated vascular cell.

15. The method of claim 14, wherein the volume comprises a tumor cell, a cancer cell, or a tumor- or cancer-associated vascular cell.

16. A method for multiplex photoacoustic imaging of a volume, the method comprising:
   (a) contacting the volume with a contrast agent comprising a plurality of radiation-absorbing components, each member of the plurality of radiation-absorbing components comprising a metallobacteriochlorin, a metallochlorin, or a combination thereof, at least one of which comprises a radiation-absorbing component selected from the group consisting of MBC-1, MBC-2, and MBC-3, wherein M is selected from the group consisting of copper and manganese;
   (b) exposing the volume to radiation with a wavelength of 650-1070 nm, wherein the radiation is calibrated to wavelengths that are differentially absorbed by the plurality of radiation-absorbing components;
   (c) differentially detecting ultrasonic waves generated in the volume by the radiation as it is differentially absorbed by the plurality of radiation-absorbing components; and
   (d) generating a photoacoustic image therefrom of the volume or a part thereof containing the administered contrast agent, wherein the photoacoustic image is generated from the differentially detecting ultrasonic waves.

17. The method of claim 16, wherein one or more of the plurality of the metallobacteriochlorins or the metallochlorins is a component of and/or encapsulated in a micelle, a liposome, a nanoparticle, or a combination thereof.

18. The method of claim 16, wherein one or more of the members of the plurality of radiation-absorbing components comprises a targeting agent, optionally wherein the targeting agent comprises a moiety that binds to a ligand and/or a target present on a tumor cell or a cancer cell, or a vascular endothelial cell associated therewith.

19. The method of claim 18, wherein the ligand and/or target comprises a tumor-associated antigen.

* * * * *